(12) United States Patent
Bader et al.

(10) Patent No.: US 7,687,646 B2
(45) Date of Patent: Mar. 30, 2010

(54) POLYMORPHIC FORMS OF OLOPATADINE HYDROCHLORIDE AND METHODS FOR PRODUCING OLOPATADINE AND SALTS THEREOF

(75) Inventors: Thomas Bader, Zürich (CH); Hans-Ulrich Bichsel, Hörhausen (CH); Bruno Gilomen, Zürich (CH); Imelda Meyer-Wilmes, Haag (CH); Mark Sundermeier, Dusseldorf (DE)

(73) Assignees: Azad Pharmaceutical Ingredients, AG, Schaffhausen (CH); Universität Zürich, Zürich (CH)

( * ) Notice: Subject to any disclaimer, the term of this patent is extended or adjusted under 35 U.S.C. 154(b) by 599 days.

(21) Appl. No.: 11/392,098

(22) Filed: Mar. 28, 2006

(65) Prior Publication Data
US 2007/0232814 A1  Oct. 4, 2007

(51) Int. Cl.
*C07D 313/10*   (2006.01)
(52) U.S. Cl. .................................................. 549/354
(58) Field of Classification Search .................. 549/354
See application file for complete search history.

(56) References Cited

U.S. PATENT DOCUMENTS

| | | | | |
|---|---|---|---|---|
| 3,354,155 | A | 11/1967 | Tretter | 260/240 |
| 3,509,175 | A | 4/1970 | Tretter | 260/333 |
| 3,681,337 | A | 8/1972 | Petree | 260/249.8 |
| 4,118,401 | A | 10/1978 | McFadden et al. | 260/333 |
| 4,160,781 | A | 7/1979 | McFadden et al. | 260/544 |
| 4,175,209 | A | 11/1979 | McFadden et al. | 562/473 |
| 4,282,365 | A | 8/1981 | Rokach et al. | 548/252 |
| 4,417,063 | A | 11/1983 | Lee et al. | 549/354 |
| 4,585,788 | A | 4/1986 | Helsley et al. | 514/450 |
| 4,871,865 | A | 10/1989 | Lever, Jr. et al. | 549/354 |
| 5,116,863 | A * | 5/1992 | Oshima et al. | 514/450 |

FOREIGN PATENT DOCUMENTS

| | | |
|---|---|---|
| DE | 2435613 | 2/1975 |
| DE | 2442060 | 5/1975 |
| DE | 2600768 | 7/1976 |
| DE | 2716230 | 10/1977 |
| DE | 3125374 | 1/1983 |
| EP | 0068370 | 1/1983 |
| EP | 0069810 | 12/1986 |
| EP | 0 351 887 A | 1/1990 |
| EP | 0214779 | 4/1990 |
| EP | 0235795 | 9/1991 |
| EP | 0235796 | 9/1997 |
| GB | 1 476 215 | 6/1977 |
| GB | 1 481 866 | 8/1977 |
| JP | 07002733 | 1/1995 |
| WO | WO 2007/119120 A2 | 10/2007 |

OTHER PUBLICATIONS

Liu et al., Zhongguo Xinyao Zazhi, 2006, 15(23), 2045-2046.*
Xue et al., Zhongguo yaowu Huaxue Zazhi, 2004, 14(6), 363-364.*
E.J. Corey et al., "Highly Reactive Equivalents of all Yliden Etriphenyl Phosphoranes for the Stereospecific Synthesis of 1,3-Dienes by Cis-Ole Fination of Hindered Aldehydes," Tetrahedron Letters, vol. 26, No. 47, 5747-5748 (1985).
Etsuo Ohshima et al., "Synthesis and Antiallergic Activity of 11-(Aminoalkylidene)-6,11-dihydrodibenz[b,e]oxepin Derivatives," J. Med. Chem. 35, 2074-2084 (1992).
Daniel E. Aultz et al., "Dibenz[b,e]oxepinalkanoic Acids as Nonsteroidal Antiinflammatory Agents. 3. ω-(6,11-Dihydro-11-oxodibenz[b,e]oxepin-2-yl)alkanoic Acids," Journal of Medicinal Chemistry, vol. 20, No. 11, 1499-1501 (1977).
Daniel E. Aultz et al., "Dibenz[b,e]oxepinalkanoic Acids as Nonsteroidal Antiinflammatory Agents. 1. 6,11-Dihydro-11-oxodibenz[b,e]oxepin-2-acetic Acids," Journal of Medicinal Chemistry, vol. 20, No. 1, 66-70 (1977).
Katsujiro Ueno et al., "6,11-Dihydro-11-oxodibenz[b,3]oxepinacetic Acids with Potent Antiinflammatory Activity," Journal of Medicinal Chemistry, vol. 19, No. 7, 941-946 (1976).
Xue et al., "Study on the Synthetic Process of a Novel Anti-Allergic Agent Olopatadine Hydrochloride," Chinese Journal of Medicinal Chemistry, vol. 14, No. 6, 2004, 363-367.
Y. Liu et al., "Synthesis of a New H1, Receptor Antagonist Olopatadine," Chinese New Drugs Journal, vol. 15, No. 23, 2006, 2045-2046.

* cited by examiner

*Primary Examiner*—D. Margaret Seaman
*Assistant Examiner*—Niloofar Rahmani
(74) *Attorney, Agent, or Firm*—Roberta L. Hastreiter; Scott B. Feder; Locke, Lord, Bissell & Liddell LLP

(57) ABSTRACT

The present invention provides a novel polymorphic form of olopatadine hydrochloride ([(Z)-3-(dimethylamino)propylidene]-6,11-dihydrodibenz[b,e]oxepin-2-acetic acid hydrochloride), a selective histamine H1-receptor antagonist that is used for the treatment of ocular symptoms of seasonal allergic conjunctivitis. The present invention also provides novel methods for producing olopatadine on a large scale, and in a manner that is cost effective, provides a low level of impurities and eliminates the need to use the costly and dangerous base, butyllithium, which is used in prior art reactions for making olopatadine. The present invention further provides novel processes for carrying out a large scale production of 3-dimethylaminopropyltriphenylphosphonium bromide and its corresponding hydrobromide salt, which are employed in the production of olopatadine, and pharmaceutically acceptable salts of olopatadine.

45 Claims, 2 Drawing Sheets

POLYMORPHIC FORMS OF OLOPATADINE HYDROCHLORIDE AND METHODS FOR PRODUCING OLOPATADINE AND SALTS THEREOF

BACKGROUND OF THE INVENTION

1. Field of the Invention

The present invention is directed to a novel polymorphic form of olopatadine hydrochloride, and to novel methods for producing olopatadine, and pharmaceutically acceptable salts thereof.

2. Background and Related Art

Olopatadine-HCl ([(Z)-3-(dimethylamino)propylidene]-6,11-dihydrodibenz[b,e]oxepin-2-acetic acid hydrochloride) is a selective histamine H1-receptor antagonist that is used for the treatment of ocular symptoms of seasonal allergic conjunctivitis. The compound may be administered in a solid oral dosage form or as an ophthalmic solution.

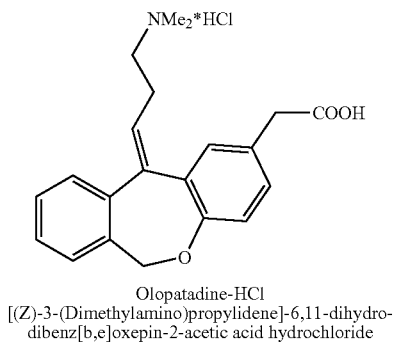

Olopatadine-HCl
[(Z)-3-(Dimethylamino)propylidene]-6,11-dihydro-dibenz[b,e]oxepin-2-acetic acid hydrochloride Olopatadine is stated to be an effective treatment for symptoms of allergic rhinitis and urticaria (e.g., sneezing, nasal discharge and nasal congestion), as well as in the treatment of various skin diseases, such as eczema and dermatitis.

Olopatadine and its pharmaceutically acceptable salts are disclosed in EP 0214779, U.S. Pat. No. 4,871,865, EP 0235796 and U.S. Pat. No. 5,116,863. There are two general routes for the preparation of olopatadine which are described in EP 0214779: One involves a Wittig reaction and the other involves a Grignard reaction followed by a dehydration step. A detailed description of the syntheses of olopatadine and its salts is also disclosed in Ohshima, E., et al., *J. Med. Chem.* 1992, 35, 2074-2084.

EP 0235796 describes a preparation of olopatadine derivatives starting from 11-oxo-6,11-dihydroxydibenz[b,e]oxepin-2-acetic acid, as well as the following three different synthetic routes for the preparation of corresponding dimethylaminopropyliden-dibenz[b,e]oxepin derivatives, as shown in schemes 1-3 below:

Scheme 1:

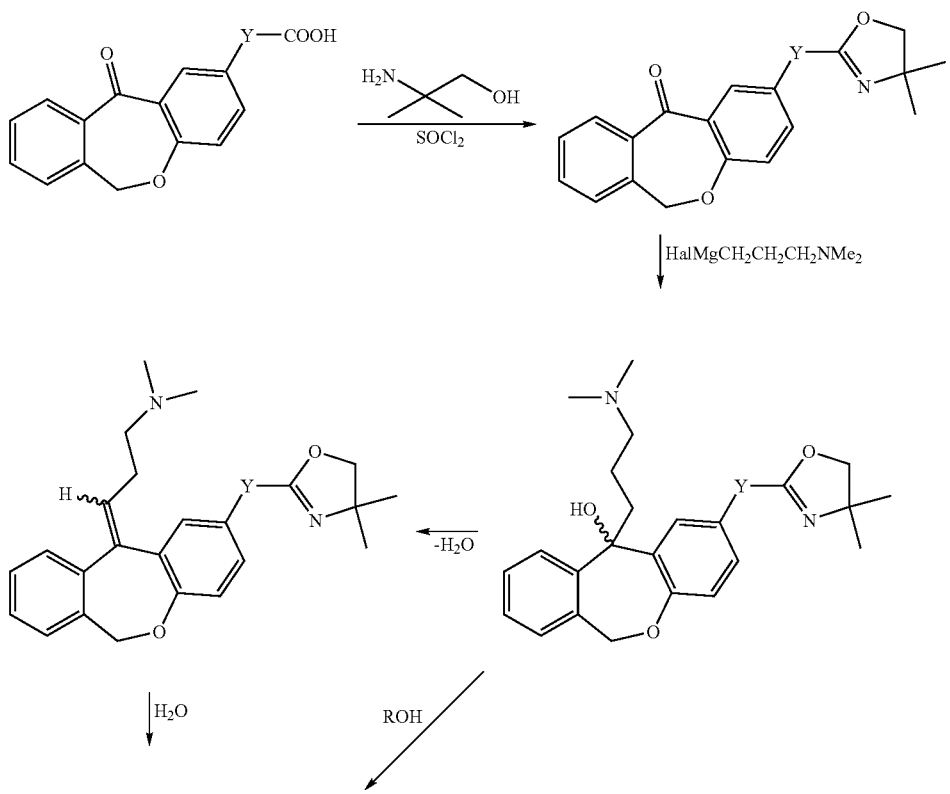

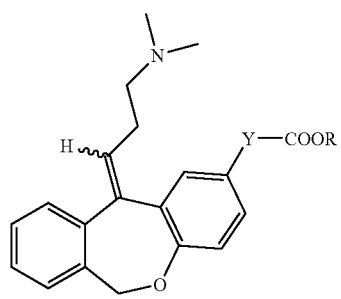
Y = —(CH$_2$)$_m$
m = 0, 1, 2, 3, 4
R = H, alkyl group
Hal = halogen
Scheme 2:
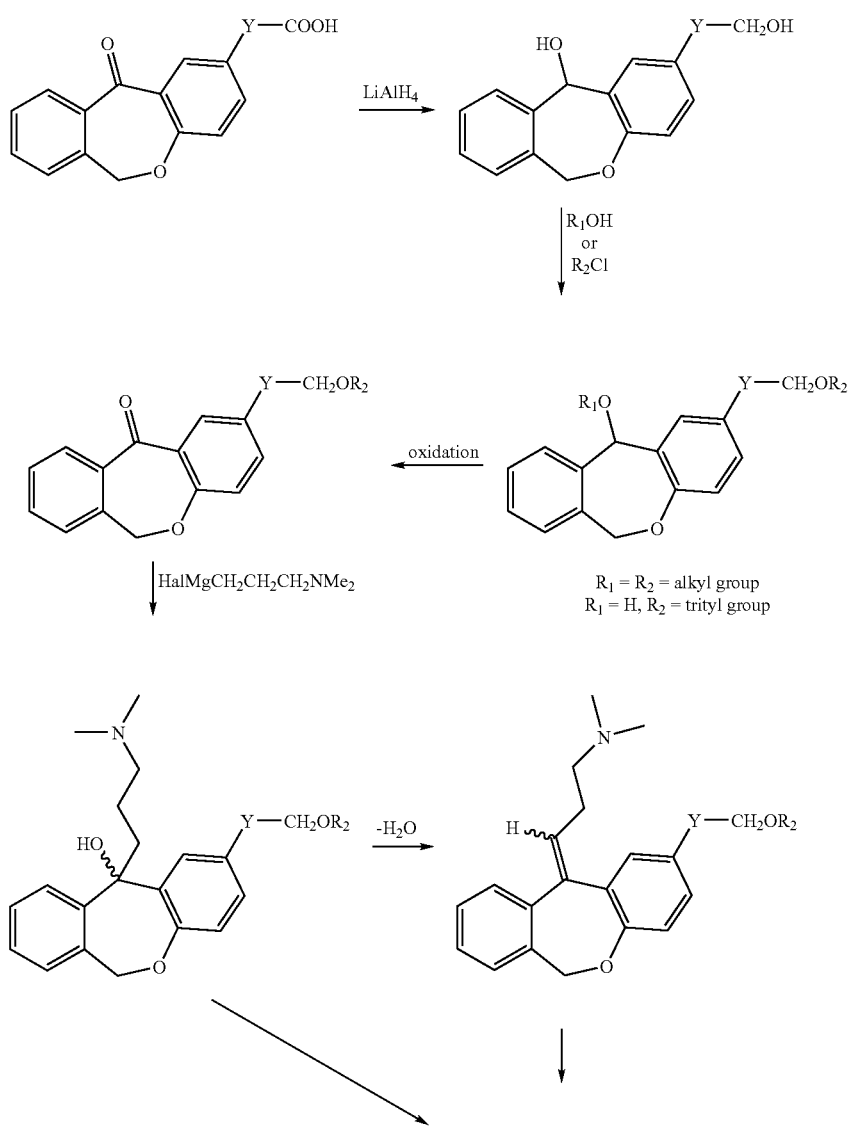

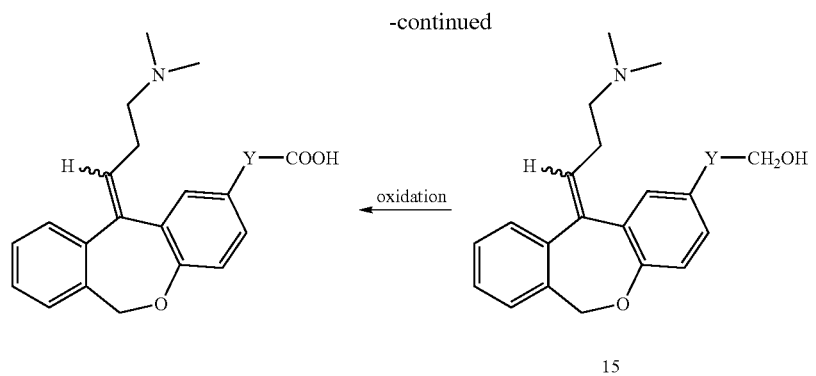

Scheme 3:

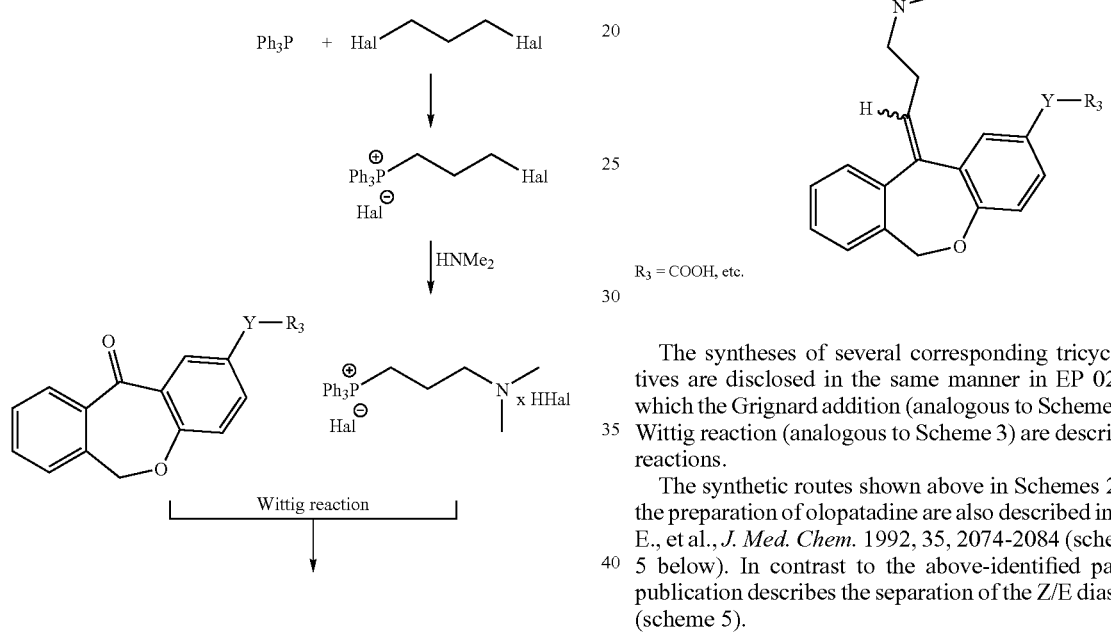

The syntheses of several corresponding tricyclic derivatives are disclosed in the same manner in EP 0214779, in which the Grignard addition (analogous to Scheme 1) and the Wittig reaction (analogous to Scheme 3) are described as key reactions.

The synthetic routes shown above in Schemes 2 and 3 for the preparation of olopatadine are also described in Ohshima, E., et al., *J. Med. Chem.* 1992, 35, 2074-2084 (schemes 4 and 5 below). In contrast to the above-identified patents, this publication describes the separation of the Z/E diastereomers (scheme 5).

Scheme 4:

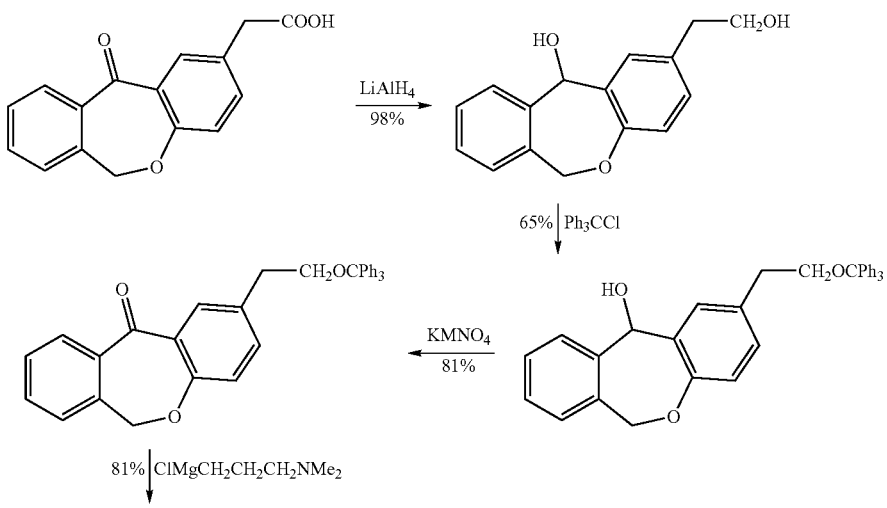

-continued
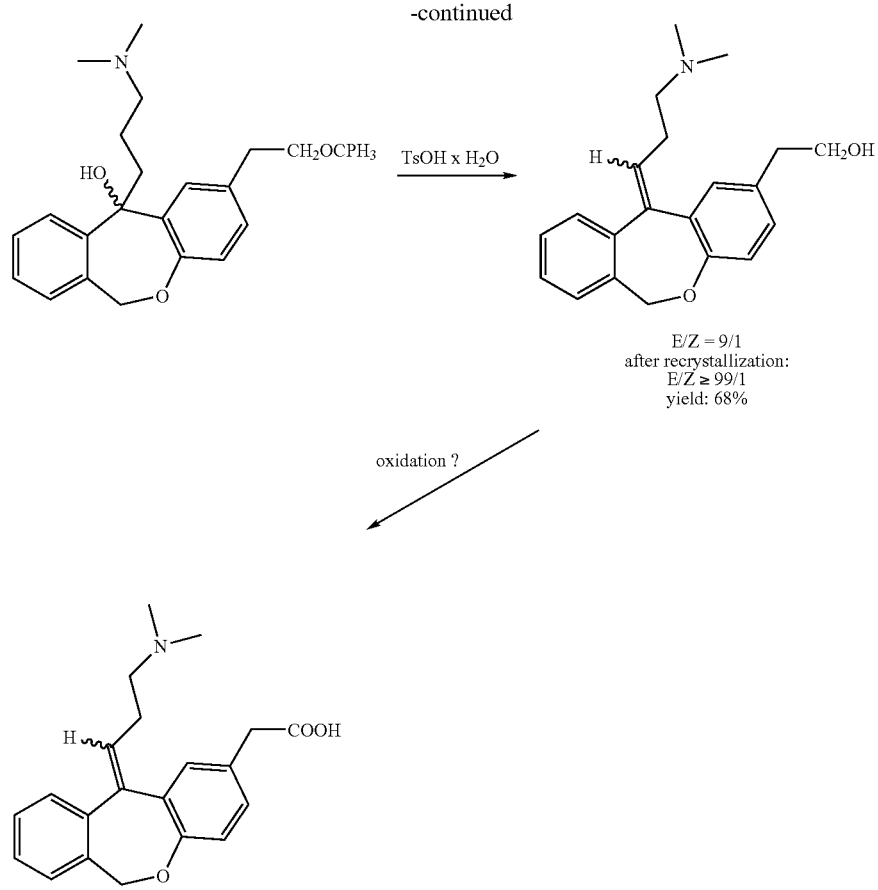
A significant disadvantage of the synthetic route depicted in Scheme 4 is the diastereoselectivity of the dehydration step, which gives up to 90% of the undesired E-isomer. The last step (oxidation) is not described in this publication.
Scheme 5 below depicts a prior art method disclosed in Ohshima, E., et al., supra.
Scheme 5:
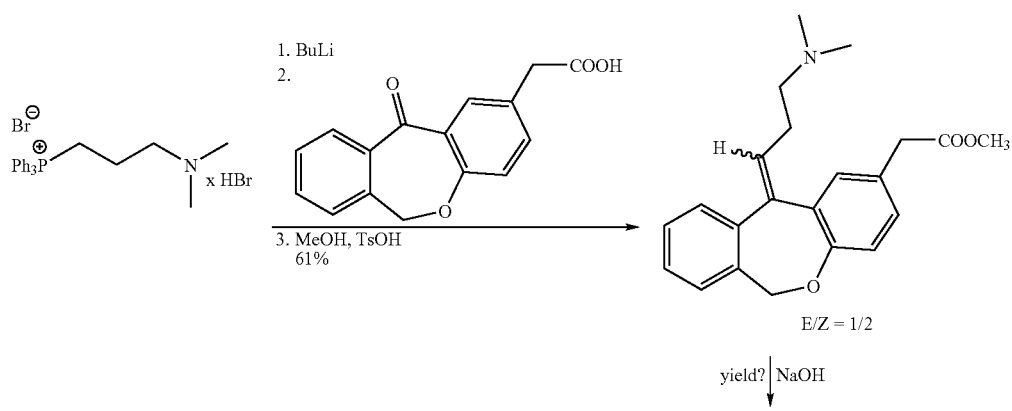

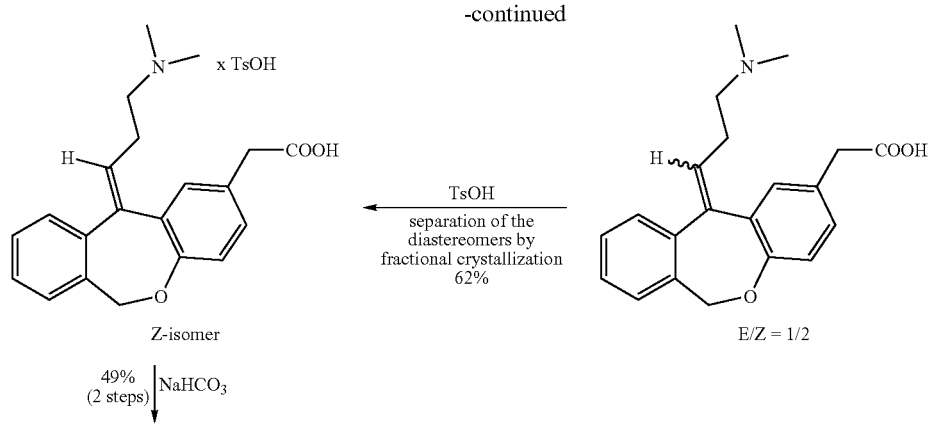

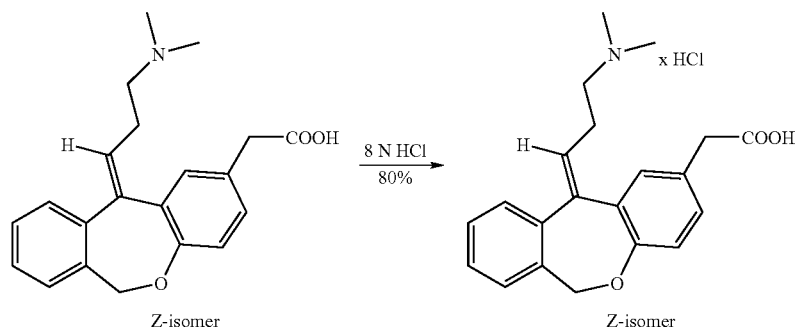

Each of the prior art methods for synthesis of olopatadine have significant cost and feasibility disadvantages. Specifically with the respect to the method set forth in Scheme 5, the disadvantages include:

(1) the need for excess reagents, e.g. 4.9 equivalents Wittig reagent and 7.6 equivalents of BuLi as the base for the Wittig reaction, which can be expensive;

(2) the need to use Wittig reagent in its hydrobromide salt form, so that additional amounts of the expensive and dangerous butyllithium reagent are necessary for the "neutralization" of the salt (i.e., excess butyllithium is required because of the neutralization);

(3) because 7.6 equivalents of the butyllithium are used (compared to 9.8 equivalents of the (Olo-IM4) Wittig reagent), the Wittig reagent is not converted completely to the reactive ylide form, and thus more than 2 equivalents of the Wittig reagent are wasted;

(4) the need for an additional esterification reaction after the Wittig reaction (presumably to facilitate isolation of the product from the reaction mixture) and the purification of the resulting oil by chromatography;

(5) the need to saponify the ester and to desalinate the reaction product (a diastereomeric mixture) with ion exchange resin, prior to separating the diastereomers;

(6) the need, after the separation of the diastereomers, and liberation of the desired diastereomer from its corresponding pTsOH salt, to desalinate the product (olopatadine) again with ion exchange resin;

(7) the formation of olopatadine hydrochloride from olopatadine is carried out using 8 N HCl in 2-propanol, which may esterify olopatadine and give rise to additional impurities and/or loss of olopatadine; and (8) the overall yield of the olopatadine, including the separation of the diastereomers, is only approximately 24%, and the volume yield is less than 1%.

As noted above, the known methods for preparing olopatadine in a Wittig reaction use the intermediate compounds 6,11-dihydro-11-oxo-dibenz[b,e]oxepin-2-acetic acid and 3-dimethylaminopropyltriphenylphosphonium bromide hydrobromide. Preparation of these chemical intermediates by prior art syntheses present a number of drawbacks that add to the cost and complexity of synthesizing olopatadine.

One known method for preparation of the compound 6,11-dihydro-11-oxo-dibenz[b,e]oxepin-2-acetic acid is depicted in Scheme 6, below. See also, U.S. Pat. No. 4,585,788; German patent publications DE 2716230, DE 2435613, DE 2442060, DE 2600768; Aultz, D. E., et al., *J. Med. Chem.* (1977), 20(1), 66-70; and Aultz, D. E., et al., *J. Med. Chem.* (1977), 20(11), 1499-1501.

Scheme 6:
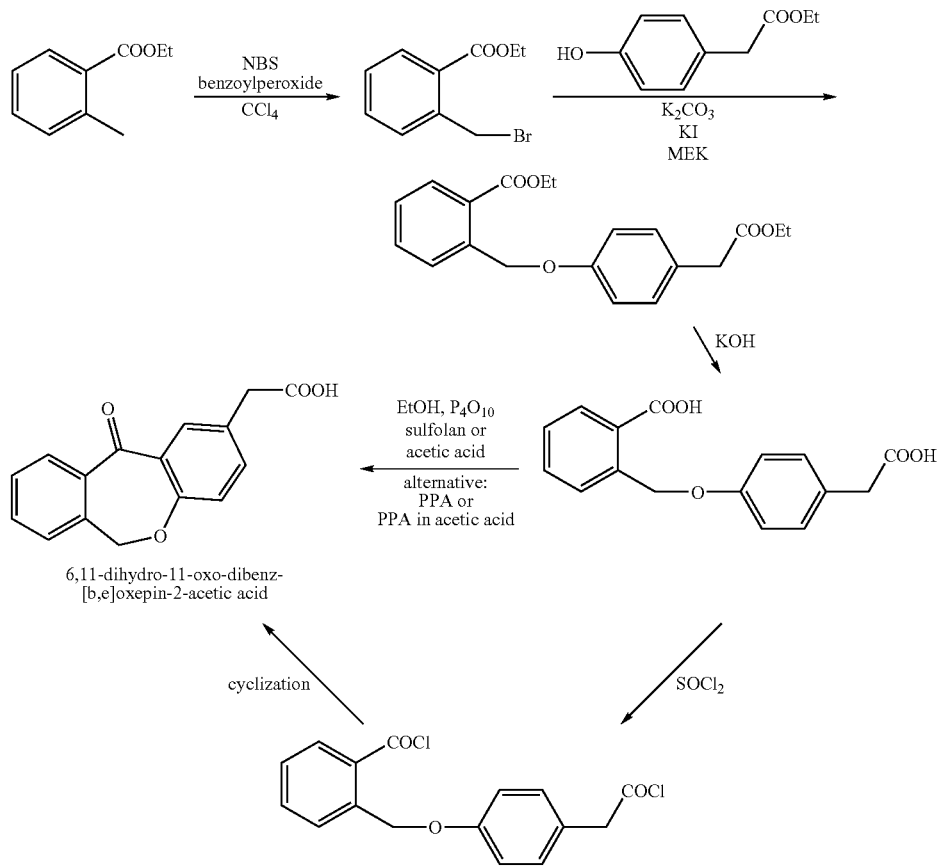
In addition, U.S. Pat. No. 4,417,063 describes another method for the preparation of 6,11-dihydro-11-oxo-dibenz[b,e]oxepin-2-acetic acid, which is shown in Scheme 7.
Scheme 7:
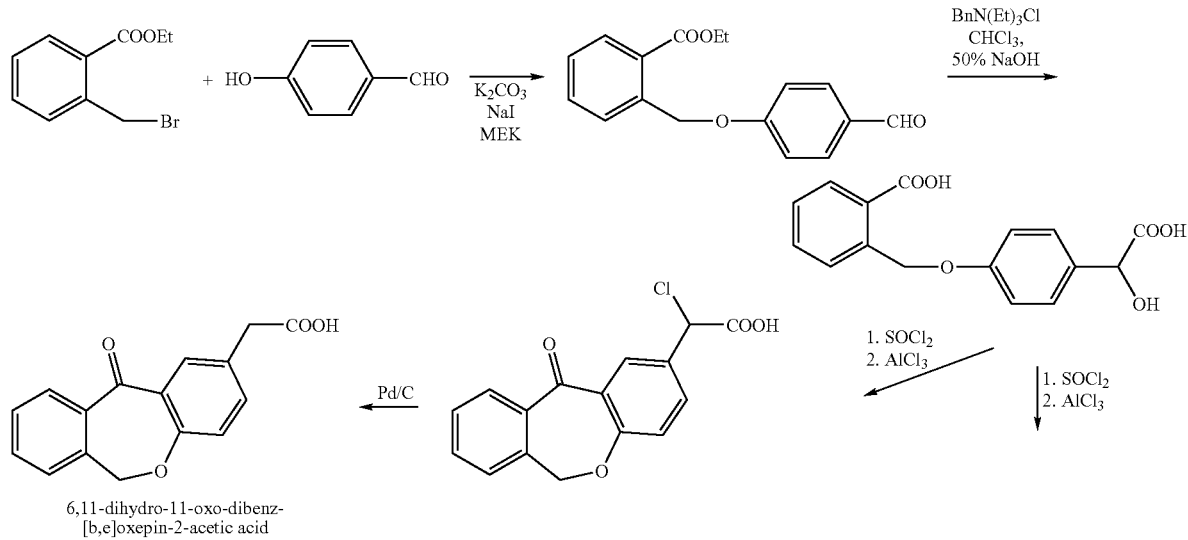

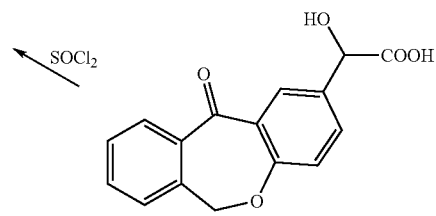

Ueno, K., et al., *J. Med. Chem.* (1976), 19(7), 941, describes yet another prior art method for preparing 6,11-dihydro-11-oxo-dibenz[b,e]oxepin-2-acetic acid, which is shown below in Scheme 8.

Scheme 8:

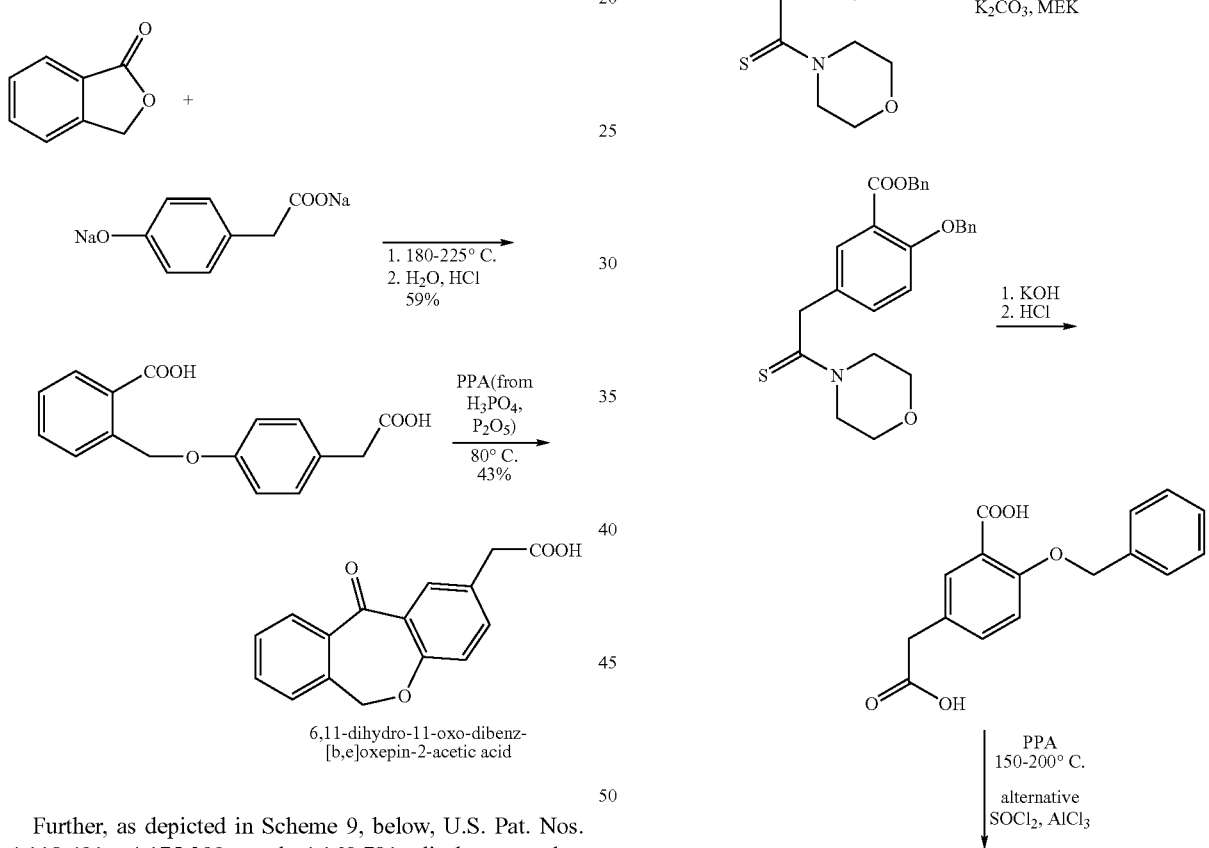

Further, as depicted in Scheme 9, below, U.S. Pat. Nos. 4,118,401; 4,175,209; and 4,160,781 disclose another method for the synthesis of 6,11-dihydro-11-oxo-dibenz[b,e]oxepin-2-acetic acid.

Scheme 9:

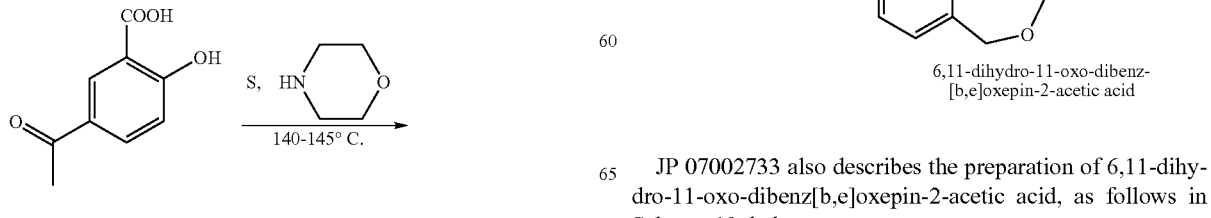

JP 07002733 also describes the preparation of 6,11-dihydro-11-oxo-dibenz[b,e]oxepin-2-acetic acid, as follows in Scheme 10, below.

Scheme 10:

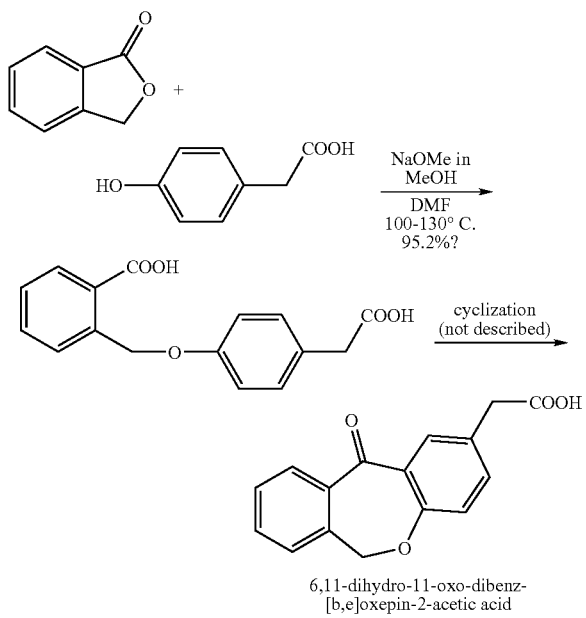

6,11-dihydro-11-oxo-dibenz-[b,e]oxepin-2-acetic acid

Specific methods and reagents for performing the intramolecular Friedel-Crafts reaction for cyclizing 4-(2-carboxybenzyloxy)-phenylacetic acid to form 6,11-dihydro-11-oxo-dibenz[b,e]oxepin-2-acetic acid are described in (1) EP 0068370 and DE 3125374 (cyclizations were carried out at reflux with acetyl chloride or acetic anhydride in the presence of phosphoric acid, in toluene, xylene or acetic anhydride as solvent); (2) EP 0069810 and U.S. Pat. No. 4,282,365 (cyclizations were carried out at 70-80° C. with trifluoroacetic anhydride in a pressure bottle); and (3) EP 0235796; U.S. Pat. No. 5,116,863 (cyclizations were carried out with trifluoroacetic anhydride in the presence of $BF_3.OEt_2$ and in methylene chloride as solvent).

Turning to the Wittig reagent for use in preparing olopatadine, 3-dimethylaminopropyltriphenylphosphonium bromide-hydrobromide and methods for its preparation are described in U.S. Pat. Nos. 3,354,155; 3,509,175; 5,116,863, and EP 0235796, and depicted in Scheme 11 below.

Scheme 11:

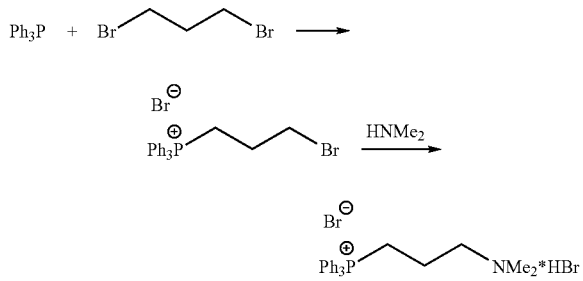

Corey, E. J., et al., *Tetrahedron Letters*, Vol. 26, No. 47, 5747-5748, 1985 describes a synthetic method for the preparation of 3-dimethylaminopropyltriphenylphosphonium bromide (free base), which is shown below in Scheme 12.

Scheme 12:

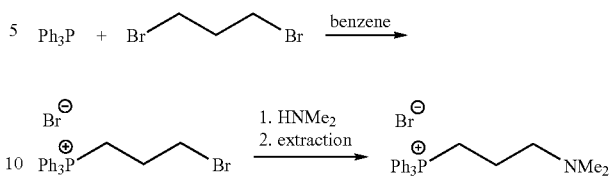

The prior art methods for preparing olopatadine and the chemical intermediates 6,11-dihydro-11-oxo-dibenz[b,e]oxepin-2-acetic acid, and 3-dimethylaminopropyltriphenylphosphonium bromide-hydrobromide (and its corresponding free base) are not desirable for synthesis of olopatadine on a commercial scale. For example, due to high reaction temperatures and the absence of solvents, the synthesis described in Ueno, K., et al., *J. Med. Chem.* (1976), 19(7), 941 and in U.S. Pat. No. 4,282,365 for preparation of the intermediate 4-(2-carboxybenzyloxy)phenylacetic acid is undesirable for a commercial scale process, although the synthesis described in JP 07002733, and set forth in Scheme 13 below, is carried out in an acceptable solvent.

Scheme 13:

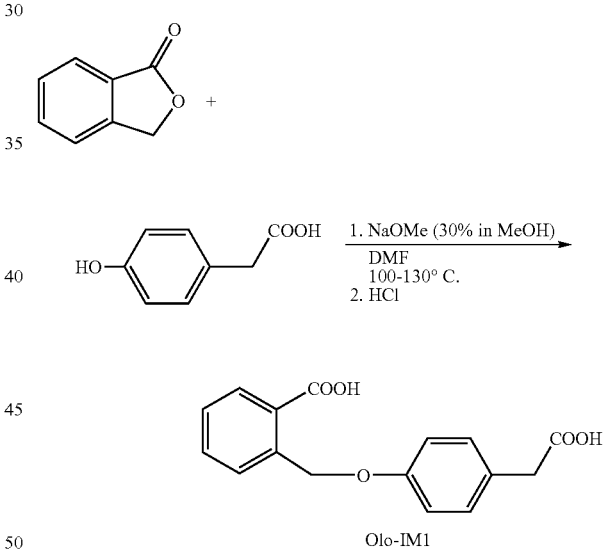

Olo-IM1

The processes described in the literature for the intramolecular Friedel-Crafts acylation used to prepare 6,11-dihydro-11-oxo-dibenz[b,e]oxepin-2-acetic acid are undesirable for commercial scale synthesis because they generally require either drastic conditions in the high boiling solvents (e.g. sulfolane) or they require a two step synthesis with the corresponding acid chlorides as intermediate. Furthermore the procedures for synthesizing 6,11-dihydro-11-oxo-dibenz[b,e]oxepin-2-acetic acid as set forth in European patent documents EP 0069810 and EP 0235796 use excess trifluoroacetic anhydride (see Scheme 14), and are carried out without solvent in a pressure bottle at 70-80° C. (EP 0069810) or at room temperature in methylene chloride using catalytic amounts of $BF_3.Et_2O$ (EP 0235796).

Scheme 14:

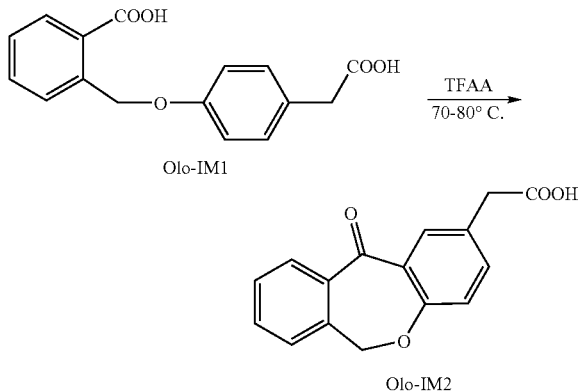

According to the teachings in EP 0235795, a suspension of 3-bromopropyltriphenylphosphonium bromide (Olo-IM4) in ethanol was reacted with 13.5 equivalents of an aqueous dimethylamine solution (50%) to provide dimethylaminopropyltriphenylphosphonium bromide HBr. After this reaction, the solvent was distilled off and the residue was recrystallized (yield: 59%).

U.S. Pat. No. 3,354,155 describes a reaction of 3-bromopropyltriphenylphosphonium bromide with 4.5 equivalents dimethylamine. The solution was concentrated and the residue was suspended in ethanol, evaporated and taken up in ethanol again. Gaseous hydrogen bromide was passed into the solution until the mixture was acidic. After filtration, the solution was concentrated, whereupon the product crystallized (yield of crude product: 85%). The crude product was recrystallized from ethanol.

A significant disadvantage of the prior art processes for making 3-dimethylaminopropyltriphenylphosphonium bromide hydrobromide involves the need for time consuming steps to remove excess dimethylamine, because such excess dimethylamine prevents crystallization of the reaction product. Thus, to obtain crystallization, the prior art processes require, for example, repeated evaporation of the reaction mixture (until dryness), which is undesirable for a commercial scale synthesis of olopatadine.

Corey, E. J., et al., *Tetrahedron Letters*, Vol. 26, No. 47, 5747-5748 (1985) describes the preparation of 3-dimethylaminopropyltriphenylphosphonium bromide (free base) from its corresponding hydrobromide salt. But the preparation of the free base, which uses an extraction step with methylene chloride as the solvent, is undesirable for commercial production because of the poor solubility of the free base in many of the organic solvents that are desirable for commercial production of chemical products, and because of the high solubility of the free base in water, causing low volume yields and loss of material. Furthermore according to this publication, the work up procedure gave an oil, which crystallized only after repeated evaporation in toluene.

It would be desirable to provide processes for preparing olopatadine on a large scale, e.g., on a commercial scale, in a manner that is cost efficient and provides olopatadine that has a low level of impurities, including a low level of the undesired diastereomer.

It further would be desirable to eliminate the need to derivatize the olopatadine product of the Wittig reaction, e.g., by esterification, in order to separate the olopatadine from the reaction mixture. It would be especially desirable to provide a method for preparing olopatadine that allows for isolation of olopatadine directly from the reaction mixture.

It would also be desirable to eliminate the need for the costly and dangerous base, butyllithium, that is used in previously described Wittig reactions for making olopatadine.

It would also be desirable to provide improved methods for preparing chemical intermediates used in the synthesis of olopatadine via a Wittig reaction.

In the description of the various aspects of applicants' invention that follows, reference may be made to the chemical intermediates, final products and byproducts in accordance with the nomenclature set forth immediately below.

The chemical names and structures for compounds that are discussed herein are set forth below in Table 1.

TABLE 1

Structures, (chemical) names and abbreviations

| Chemical name/structure | Abbreviation for Chemical name |
|---|---|
| Phthalide<br>$C_8H_6O_2$<br>Exact Mass: 134.04<br>Mol. Wt.: 134.13 | None |
| 4-Hydroxyphenylacetic acid<br>$C_8H_8O_3$<br>Exact Mass: 152.05<br>Mol. Wt.: 152.15 | None |
| 4-(2-Carboxybenzyloxy)-phenylacetic acid<br>$C_{16}H_{14}O_5$<br>Exact Mass: 286.08<br>Mol. Wt.: 286.28 | Olo-IM1 |
| 6,11-Dihydro-11-oxo-dibenz[b,e]oxepin-2-acetic acid<br>$C_{16}H_{12}O_4$<br>Exact Mass: 268.07<br>Mol. Wt.: 268.26 | Olo-IM2 |
| Triphenylphosphine<br>$Ph_3P$<br>$C_{18}H_{15}P$<br>Exact Mass: 262.09<br>Mol. Wt.: 262.29 | None |

TABLE 1-continued

Structures, (chemical) names and abbreviations

| Chemical name/structure | Abbreviation for Chemical name |
|---|---|
| 1,3.Dibromopropane<br>Br~~~Br<br>$C_3H_6Br_2$<br>Exact Mass: 199.88<br>Mol. Wt.: 201.89 | None |
| 3-Bromopropyl-triphenylphosphonium bromide<br>Br~~~Br<br>$C_3H_6Br_2$<br>Exact Mass: 199.88<br>Mol. Wt.: 201.89 | Olo-IM3 |
| 3-Dimethylaminopropyl-triphenylphosphonium bromide hydrobromide<br>$C_{23}H_{28}Br_2NP$<br>Exact Mass: 507.03<br>Mol. Wt.: 509.26 | Olo-IM4 |
| 3-Dimethylaminopropyl-triphenylphosphonium bromide<br>$C_{23}H_{27}BrNP$<br>Exact Mass: 427.11<br>Mol. Wt.: 428.34 | Olo-IM4 (free base) |
| 3-Dimethylamino-propylidene-triphenylphosphine<br>$C_{23}H_{26}NP$<br>Exact Mass: 347.18<br>Mol. Wt.: 347.43 | Olo-IM4 ylide |
| Triphenylphosphine oxide<br>$C_{18}H_{15}OP$<br>Exact Mass: 278.09<br>Mol. Wt.: 278.28 | None |

TABLE 1-continued

Structures, (chemical) names and abbreviations

| Chemical name/structure | Abbreviation for Chemical name |
|---|---|
| 3-Dimethylaminopropyl-diphenylphosphine oxide<br>$C_{17}H_{22}NOP$<br>Exact Mass: 287.14<br>Mol. Wt.: 287.34 | Olo-IM4 BP1 |
| (Z)-11-[3-Dimethylamino-propylidene]-6,11-dihydro-dibenz[b,e]oxepin-2-acetic acid<br>Olopatadine<br>$C_{21}H_{23}NO_3$<br>Exact Mass: 337.17<br>Mol. Wt.: 337.41 | Olo |
| (E)-11-[3-Dimethylamino-propylidene]-6,11-dihydro-dibenz[b,e]oxepin-2-acetic acid<br>$C_{21}H_{23}NO_3$<br>Exact Mass: 337.17<br>Mol. Wt.: 337.41 | Olo-BP1 |

TABLE 1-continued

Structures, (chemical) names and abbreviations

| Chemical name/structure | Abbreviation for Chemical name |
|---|---|
| (Z)-11-[3-Dimethylamino-propylidene]-6,11-dihydro-dibenz[b,e]oxepin-2-acetic acid hydrobromide 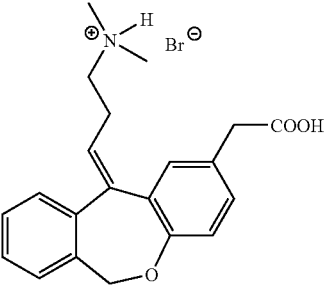 $C_{21}H_{24}BrNO_3$ Exact Mass: 417.09 Mol. Wt.: 418.32 | Olo-HBr |
| (Z)-11-[3-Dimethylamino-propylidene]-6,11-dihydro-dibenz[b,e]oxepin-2-acetic acid hydrochloride 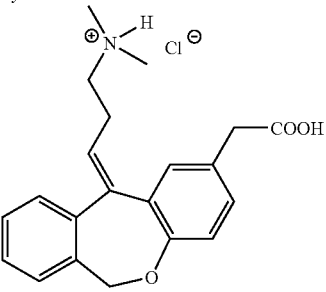 $C_{21}H_{24}ClNO_3$ Exact Mass: 373.14 Mol. Wt.: 373.87 | Olo-HCl |

DESCRIPTION OF THE INVENTION

Figure 1:
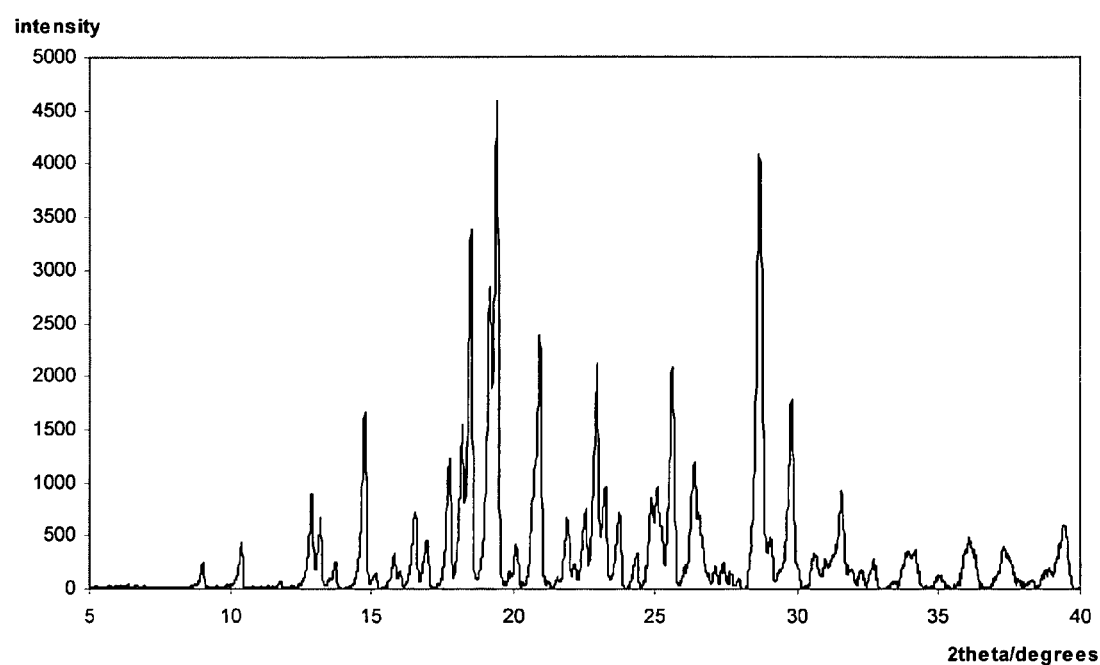
FIG. 1 is an XRD profile of the polymorphic Form B of olopatadine hydrochloride.

In one aspect, a process of the invention concerns a process for preparing olopatadine or a salt thereof, comprising:

(a) reacting 11-oxo-6,11-dihydrodibenz[b,e]oxepin-2-acetic acid, a Wittig reagent selected from the group consisting of 3-dimethylamino-propyltriphenylphosphonium halides and salts thereof, and a suitable base, under Wittig reaction conditions, to provide a reaction mixture containing olopatadine;

(b) adding an amount of water sufficient to protonate residual ylide present in the reaction mixture to provide a hydrolyzed reaction mixture;

(c) adjusting the pH of the hydrolyzed reaction mixture, or aqueous phase thereof, to a pH of about pH 12 or higher, if the reaction mixture of step (b) is not at least about pH 12, to convert excess 3-dimethylamino-propyltriphenylphosphonium halide, or salt thereof, into 3-dimethylamino-propyl-diphenylphosphine oxide;

(d) extracting the solution of step (c) with a suitable solvent to provide a solution containing a diastereomeric mixture of olopatadine and (E)-11-[3-dimethylaminopropylidene]-6,11-dihydrodibenz[b,e]oxepin-2-acetic acid and having a substantially reduced amount of 3-dimethylamino-propyldiphenylphosphine oxide;

(e) adjusting the pH of the solution obtained in step (d) to a pH between about pH 4 and pH 5 to provide acid-addition salts of olopatadine and (E)-11-[3-dimethylaminopropylidene]-6,11-dihydrodibenz[b,e]oxepin-2-acetic acid;

(f) extracting the acid-addition salts of olopatadine and (E)-11-[3-dimethylaminopropylidene]-6,11-dihydrodibenz[b,e]oxepin-2-acetic acid with a water-miscible solvent selected from the group consisting of (i) n-butanol; and (ii) mixtures of methyl-THF and a $C_1$-$C_4$ alcohol; provided that if the selected solvent is a mixture of methyl-THF and a $C_1$-$C_4$ alcohol, then the solution is evaporated and the residue is taken up in n-butanol/water;

(g) concentrating by azeotropic distillation the n-butanol/water solvent containing the acid-addition salts of olopatadine and (E)-11-[3-dimethylaminopropylidene]-6,11-dihydrodibenz[b,e]oxepin-2-acetic acid; and (h) fractionally crystallizing the acid-addition salt of olopatadine.

In another aspect, a process of the invention concerns a process for preparing olopatadine or a salt thereof, comprising:

(a) reacting 11-oxo-6,11-dihydrodibenz[b,e]oxepin-2-acetic acid, a Wittig reagent selected from the group consisting of 3-dimethylamino-propyltriphenylphosphonium halides and salts thereof, and a suitable base, under Wittig reaction conditions, to provide a reaction mixture containing olopatadine;

(b) adding an amount of water sufficient to protonate residual ylide present in the reaction mixture to provide a hydrolyzed reaction mixture;

(c) adjusting the pH of the hydrolyzed reaction mixture, or aqueous phase thereof, to a pH of about pH 12 or higher, if the reaction mixture of step (b) is not at least about pH 12, to convert excess 3-dimethylamino-propyltriphenylphosphonium halide, or salt thereof, into 3-dimethylamino-propyl-diphenylphosphine oxide;

(d) extracting the solution of step (c) with a suitable solvent to provide a solution containing a diastereomeric mixture of olopatadine and (E)-11-[3-dimethylaminopropylidene]-6,11-dihydrodibenz[b,e]oxepin-2-acetic acid and having a substantially reduced amount of 3-dimethylamino-propyldiphenylphosphine oxide;

(e) adjusting the pH of the solution obtained in step (d) to a pH of from about pH 6.5 to pH 8.0 to provide a solution containing olopatadine and (E)-11-[3-dimethylaminopropylidene]-6,11-dihydrodibenz[b,e]oxepin-2-acetic acid;

(f) extracting the solution obtained in step (e) with n-butanol to provide an n-butanol/water solution of olopatadine and (E)-11-[3-dimethylaminopropylidene]-6,11-dihydrodibenz[b,e]oxepin-2-acetic acid;

(g) adjusting the pH of the solution obtained in step (f) to a pH of from about pH 4 to about pH 5 to provide acid-addition salts of olopatadine and (E)-11-[3-dimethylaminopropylidene]-6,11-dihydrodibenz[b,e]oxepin-2-acetic acid;

(h) concentrating by azeotropic distillation the n-butanol/water solvent containing the acid-addition salts of olopatadine and (E)-11-[3-dimethylaminopropylidene]-6,11-dihydrodibenz[b,e]oxepin-2-acetic acid;

(i) fractionally crystallizing the acid-addition salt of olopatadine.

In other embodiment of the process, optionally the acid-addition salt of olopatadine may be treated with a sufficient amount of base to liberate olopatadine free base, and optionally converted from the free base to a pharmaceutically acceptable salt.

The general route for the preferred synthesis of the salt olopatadine hydrobromide (e.g., using HBr in step (e) to lower the pH to between about pH 4 and pH 5) and separation of the diastereomers is shown below in Scheme 15.

Scheme 15:

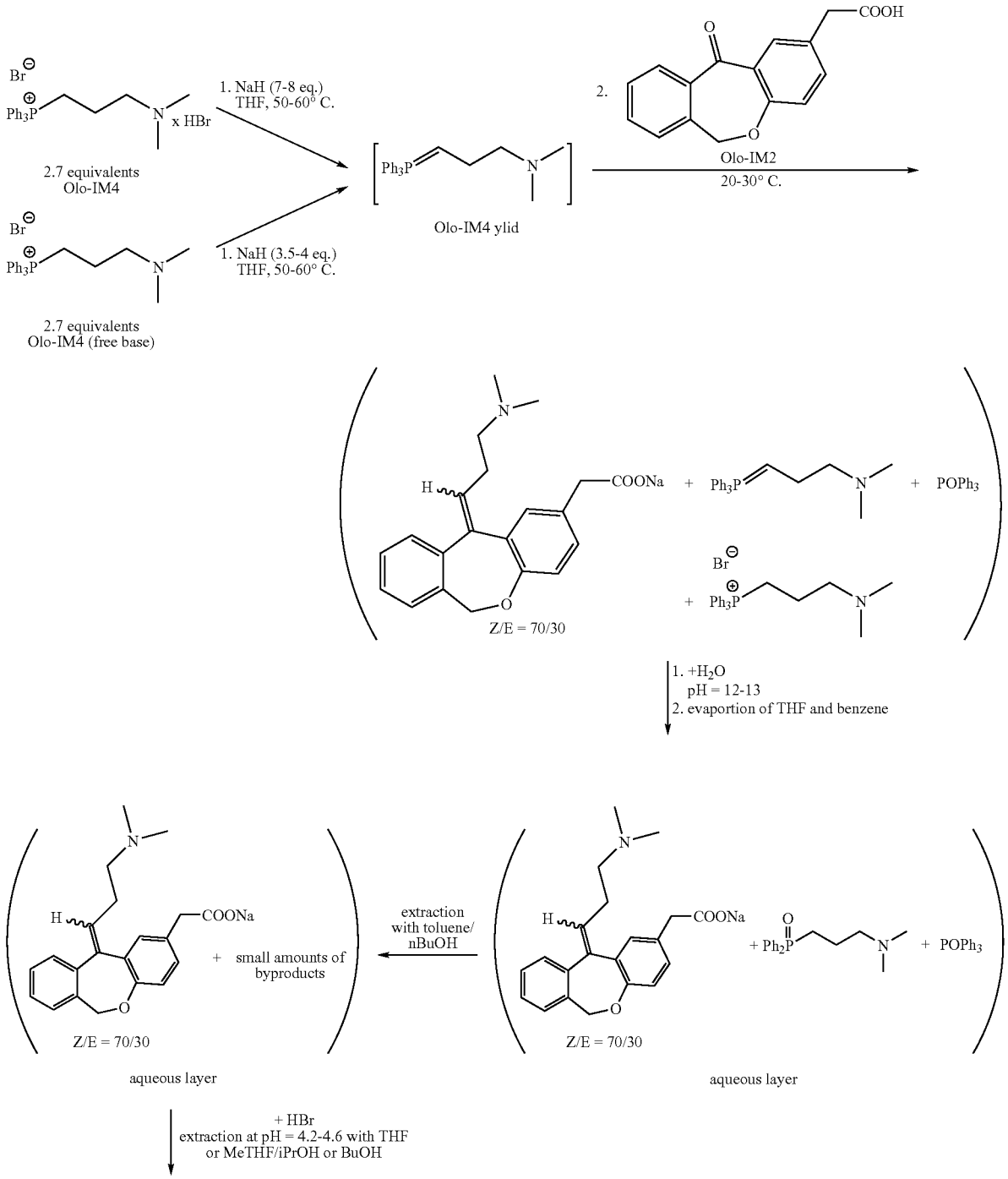

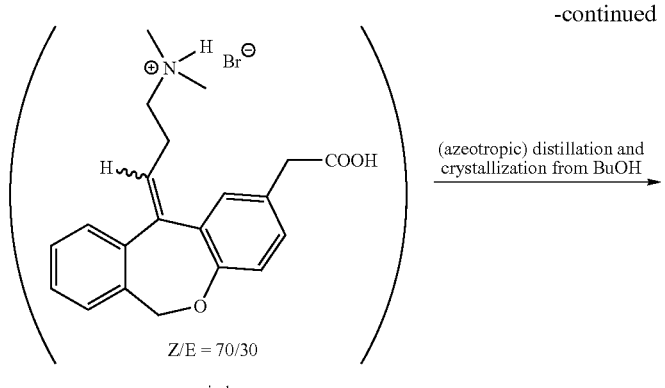
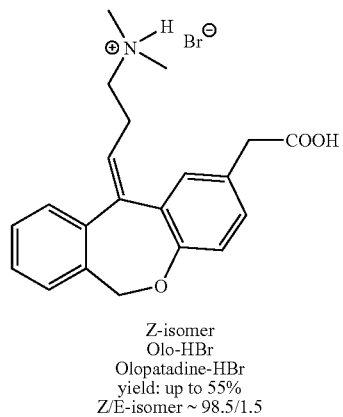

Z/E = 70/30 organic layer (azeotropic) distillation and crystallization from BuOH →

Z-isomer
Olo-HBr
Olopatadine-HBr
yield: up to 55%
Z/E-isomer ~ 98.5/1.5

It will be appreciated that the ylide is the reactive species in the Wittig reaction and may be conveniently prepared from 3-bromopropyltriphenylphosphonium bromide HBr, or its corresponding free base, or other 3-dimethylpropytriphenyphonium halides and hydrohalide salts thereof, where the halogen is bromine, chlorine or iodine. A preferred way to provide the ylide entails reacting 3-dimethylpropyltriphenylphosphonium bromide HBr (Olo-IM4), or its corresponding free base, bromopropyltriphenylphosphonium bromide (Olo-IM4 free base) with NaH in a suitable solvent under a $N_2$ atmosphere. Preferably the NaH or other base is present at a molar excess as described herein. The reaction to form the ylide preferably may be carried out at a temperature in the range of 10-70° C. A preferred reaction is carried out at a temperature in the range of 10-40° C., more preferably 20-30° C., for about 40 minutes, followed by elevating the temperature to about 40-70° C., more preferably 55-60° C., for about 3 hours. The ylide containing reaction mixture then may be cooled to a temperature below 10° C. and may be concentrated prior to initiating the Wittig reaction by careful addition of a solution of 6,11-dihydro-11-oxo-dibenz[b,e]oxepin-2-acetic acid (Olo-IM2). After addition, the reaction mixture is stirred, preferably at 20-25° C. for about 20-30 hours, then cooled to <10° C., followed by addition of water to quench the reaction. Suitable solvents for carrying out the Wittig reaction, including the step of ylide formation, include anhydrous solvents such as tetrahydrofuran (THF), dimethylformamide (DMF), N-methylpyrrolidone (NMP) and toluene.

We have found that the dangerous and expensive butyllithium reagent, which is used in the prior art reactions, can be advantageously replaced with sodium hydride (NaH). Alternative bases including LiH, NaOtBu, NaOtPent, KOtBu, NaOMe, NaOEt, and KHMDS, as well as mixtures of these bases, even when used in various solvents including THF, DMF, NMP and toluene, and mixtures thereof, were found to be substantially inferior to either butyllithium or NaH. Bases other than butyllithium and NaH resulted in incomplete conversion, isomerization of olopatadine into the undesired (E)-diastereomer (especially if the base was used in excess) or the formation of numerous byproducts.

We have found that within 30 hours at room temperature a reaction using about 2.7 equivalents of 3-dimethylaminopropyltriphenylphosphonium bromide hydrobromide (Olo-IM4) and not more than about 7-8 equivalents of NaH gave an almost quantitative conversion of 6,11-dihydro-11-oxo-dibenz[b,e]oxepin-2-acetic acid (Olo-IM2) to a diastereomeric mixture of olopatadine with a (Z)/(E) ratio of about 70:30. Use of the free base, 3-dimethylaminopropyltriphenylphosphonium bromide, requires only about 3.5-4 equivalents of NaH. See Scheme 16 below. The reaction yield for the (Z)-isomer was up to 67%. The novel Wittig reaction using NaH is stable and robust. Neither excess NaH, nor higher temperatures (up to 30° C.), were found to have an adverse influence on the selectivity and yield of the reaction.

The ylide is formed almost quantitatively by heating a mixture of NaH and the Wittig reagent (3-dimethylaminopropyltriphenylphosphonium bromide or its corresponding hydrobromide salt) in THF for 2.5 to 3 hours at 55-60° C. Then, 6,11-dihydro-11-oxo-dibenz[b,e]oxepin-2-acetic acid (Olo-IM2) may be added to the orange mixture and the suspension stirred at room temperature. The addition of 6,11-dihydro-11-oxo-dibenz[b,e]oxepin-2-acetic acid to the ylide causes a partial protonation of the ylide, although the excess NaH which is present may regenerate the ylide form.

Scheme 16:

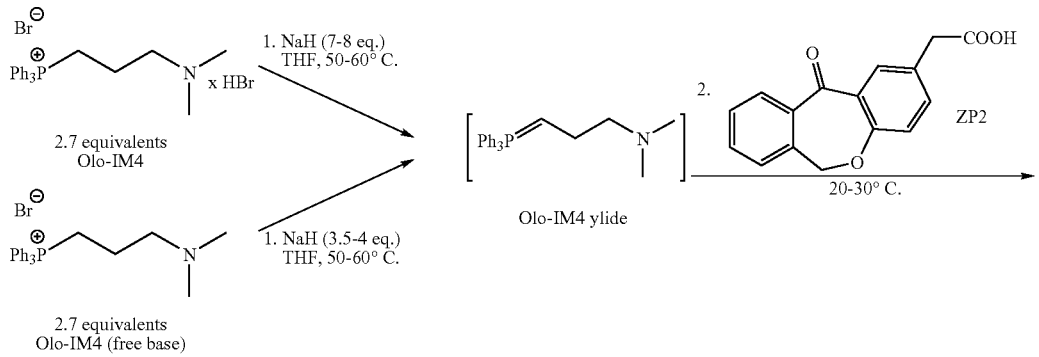

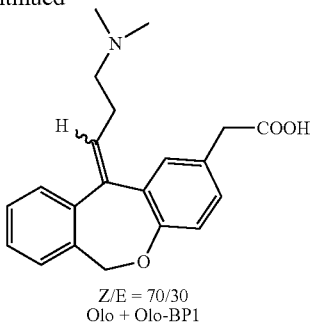

Z/E = 70/30
Olo + Olo-BP1

While it is preferred to form the 3-dimethylamino-propylidene-triphenylphosphine (Olo-IM4 ylide), prior to the addition of 6,11-dihydro-11-oxo-dibenz[b,e]oxepin-2-acetic acid, if the Wittig reaction is carried out for instance by mixing and stirring of NaH, Wittig reagent, and 6,11-dihydro-11-oxo-dibenz[b,e]oxepin-2-acetic acid (Olo-IM2) in THF at room temperature, then the reaction may be carried out over the course of 5-6 days. The prolonged stirring time is probably caused by limited solubility of both the Wittig reagent and NaH in THF.

Among the several advantageous features of the inventive processes is the process for separating olopatadine from unreacted Wittig reagent (see steps (c) and (d) in the above process). In accordance with this aspect of the inventive process, after the addition of water to quench the reaction mixture, the pH of the reaction mixture has (or is adjusted to) a pH of 12 or greater, which converts unreacted Wittig reagent to 3-dimethylaminopropyldiphenylphosphine oxide and triphenylphosphine oxide. A sufficient molar excess of NaH (or other suitable base) may be used in the Wittig reaction so that when water is added to quench the reaction, the remaining base provides the pH of 12 or above. If the pH of the reaction mixture is less than pH 12, any suitably strong base, such as NaOH may be used to raise the pH to 12 or above.

Hydrolysis of the excess NaH in the olopatadine-containing reaction mixture at a pH of about pH 12-13 provides an almost complete conversion of 3-dimethylaminopropyltriphenylphosphonium bromide (Olo-IM4 free base) and 3-dimethylaminopropylidenetriphenylphosphine (Olo-IM4 ylide) into the byproducts 3-dimethylaminopropyldiphenylphosphine oxide (Olo-IM4 BP1) and triphenylphosphine oxide, which byproducts may be extracted almost quantitatively (at pH 12-13) with negligible loss (≦2%) of olopatadine.

Scheme 17:

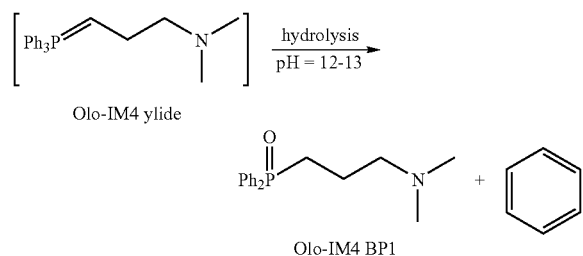

Olo-IM4 ylide

Olo-IM4 BP1

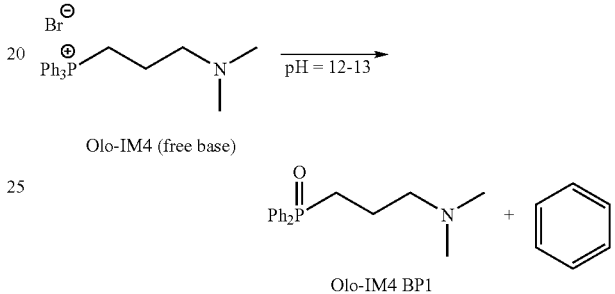

Olo-IM4 (free base)

Olo-IM4 BP1

One or more extractions of the 3-dimethylaminopropyldiphenylphosphine oxide and triphenylphosphine oxide byproducts from the reaction mixture may be carried out using a suitable solvent in which the solubility of 3-dimethylaminopropyldiphenylphosphine oxide and triphenylphosphine oxide is high, relative to the solubility of olopatadine. Preferred solvents include toluene or mixtures of toluene and n-butanol. A presently preferred solvent is toluene:n-butanol (9:1).

After one or more extractions to remove the byproducts so that they are substantially reduced in concentration, a sufficient amount of acid is added to the olopatadine containing solution to reduce the pH to pH 8 or less, and the olopatadine and its diastereomer (as acid-addition salts or "free amino acids") are extracted. In a preferred embodiment, HBr is added to bring the pH to between about pH 4 and 5, more preferably to between pH 4.2 and pH 4.6 to provide olopatadine and its diastereomer as hydrobromide salts. In another embodiment, acid is added to bring the pH to between about pH 6.5 and about pH 8, preferably between pH 6.8 and pH 7.2, and the olopatadine and its diastereomer (in their free amino acid form) are extracted into n-butanol and then acidified with HBr to between about pH 4 and 5, more preferably to between pH 4.2 and pH 4.6.

It is presently preferred to acidify the mixture of olopatadine and the diastereomeric (E)-11-[3-dimethylaminopropylidene]-6,11-dihydrodibenz[b,e]oxepin-2-acetic acid to form their corresponding acid-addition salts. It will be understood that adjusting the pH to about 4.2-4.6 with hydrobromic acid provides a diasteromeric mixture as the hydrobromide salts, whereas adjusting the pH with hydrochloric acid provides the diastereomeric mixture as mixed (hydrochloride/hydrobromide) salts. Other acids which form acid-addition salts with olopatadine may also be used. The diastereomeric mixture of salts then may be extracted into an organic solvent suitable for providing a water-containing organic layer. Suitable organic solvents for the extraction of the diastereomeric mixture of acid-addition salts include n-butanol, mixtures of 2-methyltetrahydrofuran and a $C_1$-$C_4$ alcohol, preferably 2-methyltetrahydrofuran and 2-propanol, and THF (after saturating the aqueous layer with NaCl or other suitable salt). It is most preferred to use n-butanol. If a solvent other than n-butanol is used in the extraction step, the organic layer (containing water) may then be evaporated at reduced pressure, for example at between about 200 mbar and 500 mbar, and then diluted with n-butanol.

In a further aspect of the present invention, we have found that a desirable yield of olopatadine salt may be obtained when fractional crystallization of a diastereomeric mixture dissolved or suspended in n-butanol (containing water) is carried out at a pH significantly below the isoelectric point of olopatadine. In fact, compared to the crystallization of an olopatadine salt, e.g., olopatadine HBr at, between pH 4.2 and pH 4.6. isolation of the so-called "free amino acid" form of olopatadine present at the isoelectric point (e.g., pH 6.8-7.2) either by direct crystallization from the water layer, or by extraction and subsequent fractional crystallization, undesirably resulted in low yields, partially in combination with insufficient selectivities during the fractional crystallizations, and/or formation of resinous precipitates that could not be filtered off.

Fractional crystallization of a diastereomeric composition of olopatadine and (E)-11-[3-dimethylaminopropylidene]-6,11-dihydrodibenz[b,e]oxepin-2-acetic acid, as acid-addition salts most preferably dissolved or suspended in n-butanol (containing water), was unexpectedly found to provide crystalline olopatadine salt having an improved (Z)/(E) ratio. Fractional crystallization of the olopatadine and (E)-11-[3-dimethylaminopropylidene]-6,11-dihydrodibenz[b,e]oxepin-2-acetic acid (as acid-addition salts) may be readily achieved by azeotropic distillation. Typically the butanol/water solvent consists initially of about 10-20% water. Most preferably the olopatadine salt is present as a hydrobromide salt, a hydrochloride salt or a mixture of the two salts. Azeotropic distillation may be carried out to initialize crystallization. Fractional crystallization provides a (Z)/(E) ratio that is enhanced relative to the starting ratio of the diastereomeric mixture of olopatadine salt. The suspension of olopatadine salt is then stirred while cooling to (and maintaining at) room temperature over a period of about 1 to about 20 hours, preferably about 16 hours. The final water content of the crystallization solvent after fractional crystallization should be between 0.5% and 5%, preferably between 1% and 4% water, at which point the resulting olopatadine salt typically has a diastereomeric (Z)/(E) ratio of from about 86/14 to 90/10 or greater. While not intending to be bound by theory, it appears that the enhanced (Z)/(E) ratio may be attributed to the fact that the diastereomeric mixture is easily soluble in aqueous nBuOH having a water content of about 10%-20%, whereas the solubility of these salts in anhydrous/dry nBuOH is very low. The solubility of the diastereomeric mixture comprising olopatadine is also low in water at pH=4.2-4.6.

It has also been discovered that the (Z)/(E) isomer ratio of an olopatadine salt, such as olopatadine hydrobromide having an initial (Z)/(E) ratio of about 86/14 or greater can be further enriched by suspending the olopatadine salt in n-butanol having a water concentration of at least about 0.2%, and more preferably from about 2-4% water. The slurry may be stirred for about 0.5 to about 2 hours, preferably about 1 hour, at an elevated temperature, preferably about 80° C. and then cooled to room temperature and stirred for up to an additional 16 hours or more. Preferably, the olopatadine salt is olopatadine hydrobromide or olopatadine hydrochloride or a mixture thereof. Using the hydrobromide salt, the slurrying conditions have been discovered to provide a significant increase in the (Z)/(E) ratio up to about 99:1 or greater.

The olopatadine salt may be converted to its free base form by reaction with a strong base, preferably NaOH, in suitable solvent, preferably water at room temperature for a period from about 1 to about 20 hours, e.g., about 16 hours, advantageously with consequent increase in the (Z)/(E) ratio. The olopatadine free base may then be optionally converted into a pharmaceutically acceptable salt of olopatadine by reacting the olopatadine free base with an acid to provide e.g., a corresponding HCl, HBr, acetate, tosylate, mesylate or other pharmaceutically acceptable salt as known in the art, advantageously with further increase in the (Z)/(E) ratio up to about 99.9/0.1. The presently preferred salt is the HCl salt.

As shown in Scheme 18 below, to prepare olopatadine hydrochloride (Olo-HCl), from olopatadine hydrobromide, the hydrochloride salt was suspended in water and the pH was adjusted to 6.8-7.2. During the neutralization, a solution was obtained for a short time and then the free amino acid was crystallized. Afterwards, the free amino acid was treated in an organic solvent with concentrated hydrochloric acid to give the corresponding hydrochloride salt (overall yield of olopatadine hydrochloride: 50-52% based on Olo-IM2; volume yield up to 4-5%).

Scheme 18:

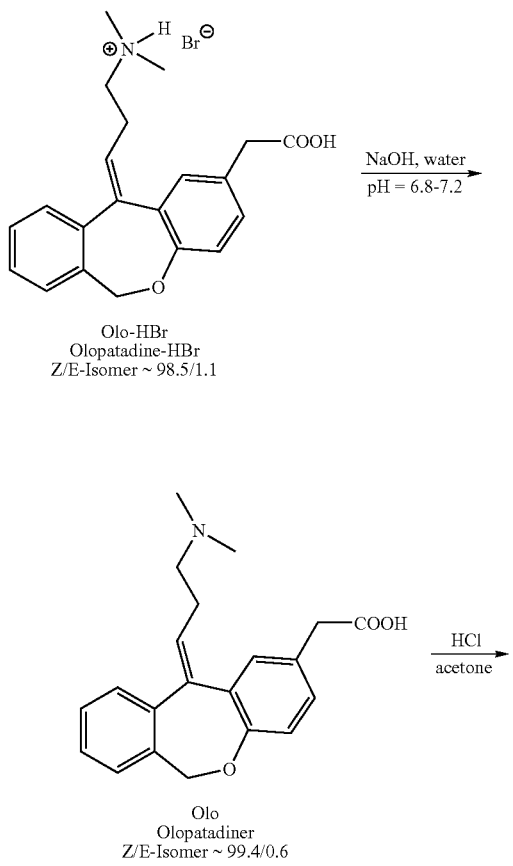

Olo-HBr
Olopatadine-HBr
Z/E-Isomer ~ 98.5/1.1

Olo
Olopatadiner
Z/E-Isomer ~ 99.4/0.6

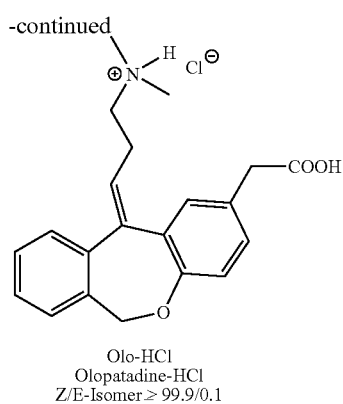

Olo-HCl
Olopatadine-HCl
Z/E-Isomer ≥ 99.9/0.1

Although the above description has been set forth with respect to a comprehensive synthesis and purification of olopatadine beginning with a Wittig reaction and continuing through formation of a pharmaceutically acceptable salt of olopatadine in highly pure form, additional inventive aspects reside within combinations of the individuals steps as well as in preparation of various reactants.

Thus, another aspect the invention described above concerns a novel Wittig reaction for preparing olopatadine, comprising the steps of:

(a) combining a 3-dimethylpropyltriphenylphosphonium halide hydrohalide, or a corresponding free base thereof, and sodium hydride in a suitable solvent to provide a reaction mixture containing the ylide, 3-dimethylaminopropylidenetriphenylphosphine;

(b) combining the reaction mixture containing the ylide with 6,11-dihydro-11-oxo-dibenz[b,e]oxepin-2-acetic acid under Wittig reaction conditions to provide a diastereomeric mixture comprising olopatadine.

In a further aspect, the invention involves a process for preparing olopatadine, comprising the steps of:

(a) providing a Wittig reaction mixture comprising a diastereomeric mixture containing olopatadine;

(b) adding an amount of water sufficient to protonate residual ylide remaining in the reaction mixture;

(c) adjusting, if necessary, the pH of the olopatadine-containing hydrolyzed reaction mixture, or aqueous phase thereof, to a pH of about pH 12 or higher such that excess 3-dimethylamino-propyltriphenylphosphonium halide, or salt thereof, is converted into 3-dimethylamino-propyldiphenylphosphine oxide; and (d) extracting the solution of step (c) with a suitable solvent to provide a solution containing a diastereomeric mixture of olopatadine and (E)-11-[3-dimethylaminopropylidene]-6, 11-dihydrodibenz[b,e]oxepin-2-acetic acid that is substantially free of 3-dimethylaminopropyldiphenylphosphine oxide and triphenylphosphine.

In still a further aspect, the invention entails a process for enriching the (Z)/(E) ratio of a diastereomeric mixture containing a salt of olopatadine comprising the steps of:

(a) providing a butanol/water suspension of olopatadine and (E)-11-[3-dimethylamino-propylidene]-6,11-dihydrodibenz[b,e]oxepin-2-acetic acid, as acid-addition salts, wherein the initial (Z)/(E) ratio is at least about 86/14; and (b) fractionally crystallizing the suspension by azeotropic distillation to provide crystalline olopatadine salt having a (Z)/(E) ratio greater than the initial (Z)/(E) ratio.

In a further aspect, the invention involves a process for enriching the (Z)/(E) ratio of a diastereomeric mixture containing a salt of olopatadine, comprising the steps of:

(a) suspending in butanol/water a diastereomeric mixture containing an olopatadine salt; and (b) stirring the suspension for an amount of time sufficient to increase the percentage of suspended olopatadine salt, relative to its diastereomer.

Each of these combinations of process steps is described above and exemplified in the Examples below.

Turning now to the processes for making certain starting materials used in preparing olopatadine, in yet another of its aspects, the invention involves a novel reaction for the preparation of 6,11-dihydro-11-oxo-dibenz[b,e]oxepin-2-acetic acid (Olo-IM2) in an intramolecular Friedel-Crafts reaction of 4-(2-carboxybenzyloxy)-phenylacetic acid (Olo-IM1). The reaction advantageously can be carried out at moderate temperatures of from about 20° C. to about 40° C., preferably from about 20° C. to about 25° C., in a suitable inert aromatic solvent, such as a substituted or nonsubstituted aromatic solvent, wherein the substituents are selected from the group of alkyl, halo, or nitro. A preferred solvent is toluene, in which solvent the Friedel-Crafts reaction proceeds without competitive adverse reactions with the aromatic solvent, and almost quantitatively within about one hour using only from about 1.1 to about 1.2 equivalents of trifluoroacetic anhydride in the presence of catalytic amounts of trifluoromethanesulfonic acid or $BF_3.Et_2O$. (See Scheme 19.)

Scheme 19:

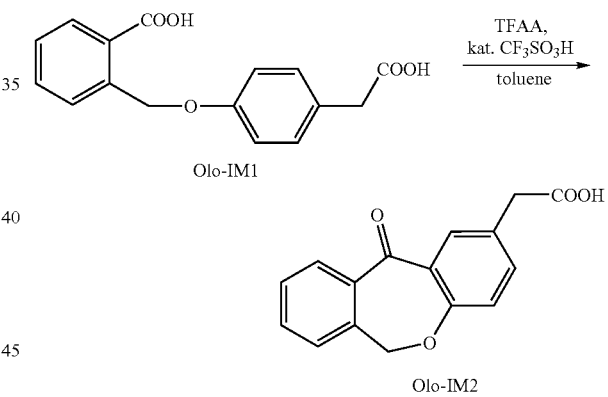

The 6,11-dihydro-11-oxo-dibenz[b,e]oxepin-2-acetic acid (Olo-IM2) is subsequently reacted with 3-dimethylaminopropyltriphenylphosphonium bromide hydrobromide ("Olo-IM4") in the reaction scheme leading to production of olopatadine.

A novel and nonobvious process has been discovered in which large scale production of 3-dimethylaminopropyltriphenylphosphonium bromide hydrobromide (Olo-IM4) may be carried out while avoiding the large excess of dimethylamine required by the prior art processes. The inventive process allows for the direct crystallization of 3-dimethylaminopropyltriphenylphosphonium bromide hydrobromide (Olo-IM4) from the reaction mixture.

Thus, in another of its aspects the invention involves a process for preparing 3-dimethylaminopropyltriphenylphosphonium bromide hydrobromide (Olo-IM4) which comprises, (a) reacting 3-bromopropyltriphenylphosphonium bromide (Olo-IM3) with dimethylamine to provide Olo-IM4; and (b) sequestering sufficient residual dimethylamine so that 3-dimethylaminopropyltriphenylphosphonium bromide hydrobromide may be crystallized directly from the reaction mixture. Preferably the reaction is carried out with a 3-4 fold molar excess of dimethylamine.

Among the compounds capable of sequestering dimethylamine so that the reaction product may crystallize directly from the reaction mixture are acetyl halides, phosphorus oxyhalides, cyanuric halides, sulfuryl halides, such as acetyl bromide, phosphorus oxybromide, cyanuric bromide, sulfuryl bromide, and the like. Scheme 20, below, shows the reaction for preparing 3-dimethylaminopropytriphenylphosphonium bromide hydrobromide (Olo-IM4), wherein the product is crystallized directly from the reaction mixture after the addition of acetyl bromide.

Additionally, as is generally known, the identity of the halide counterion from the phosphonium halide has little effect on the outcome of the Wittig reaction. Therefore, the preparation of dimethylaminopropytriphenylphosphoniumchloride hydrochloride would also generate the corresponding free base, and a hydrogen chloride-generating sequestering agent, e.g., acetyl chloride, may be used to remove excess dimethylamine.

Scheme 20:

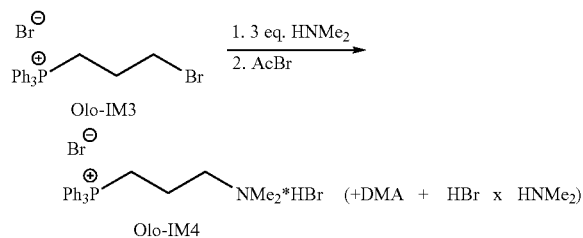

The crude 3-dimethylaminopropyltriphenylphosphonium bromide hydrobromide (Olo-IM4) product may be filtered off directly, and then readily recrystallized from ethanol or other suitable solvent to give almost pure product with a yield exceeding 85% for the recyrstallization step. The novel process advantageously eliminates the need to repeatedly distill/remove the solvent (and residual solvent) and excess dimethylamine from solutions of the Olo-IM4 product, as required by the prior art methods to obtain a crystalline material of suitable purity.

In another aspect, the invention involves a process for preparing 3-dimethylaminopropytriphenylphosphonium bromide free base (Olo-IM4 free base) comprising the step of combining in a suitable solvent, 3-dimethylaminopropytriphenylphosphonium bromide hydrobromide and an alkaline earth metal carbonate or alkali metal carbonate. The novel process liberates Olo-IM4 free base from its corresponding hydrobromide salt, as shown in Scheme 21 below, allowing for simplified production of this free base on a large scale.

Scheme 21:

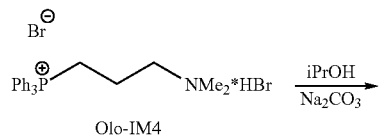

-continued

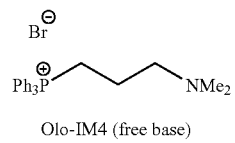

Olo-IM4 (free base)

The process for liberating 3-dimethylaminopropyltriphenylphosphonium bromide (free base) from its corresponding hydrobromide salt proceeds at temperatures >50° C., and preferably uses sodium carbonate or potassium carbonate as base. Suitable solvents for the process include alcohols, such as $C_1$ to $C_4$ alcohols, acetonitrile or these solvents with water. After the reaction, the salt may be filtered off, the water (if present) removed, and the filtrate concentrated to initiate crystallization of the free base. Crystallization may be completed by the addition an antisolvent such as MTBE or cyclohexane or a mixture thereof, in a ratio of up to 1:2 MTBE:cyclohexane, preferably in a ratio of about 1:1 MTBE:cyclohexane to provide Olo-IM4 (free base) in yields of about 95%. It is preferred, however, not to use cyclohexane to complete the crystallization where the solvent used in the reaction is methanol or acetonitrile.

For the direct preparation of Olo-IM4 free base from 3-bromopropyltriphenylphosphonium bromide (Olo-IM3), the 3-bromopropyltriphenylphosphonium bromide may be first reacted with dimethylamine, e.g., a solution of dimethylamine in ethanol or gaseous dimethylamine dissolved in 2-propanol as solvent, followed by treating the reaction mixture with potassium carbonate, stirring the suspension at about 45° C., filtering, concentrating and crystallizing completely by addition of MTBE (and cyclohexane) or toluene. Yields up to about 93% may be obtained.

Scheme 22:

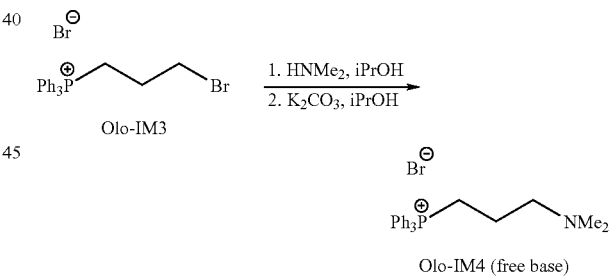

Olo-IM4 (free base)

Olopatadine and pharmaceutically acceptable salts of olopatadine may be formulated in pharmaceutically acceptable compositions for administration. Pharmaceutical compositions made using olopatadine or a salt thereof are useful for topical ophthalmic administration and can be made using known techniques. Ophthalmically acceptable excipients, such as tonicity-adjusting agents, pH-adjusting agents, buffering agents, preservatives, comfort enhancing agents, viscosity-modifying agents, stabilizing agents, etc. may be included. Isotonic agents that may be used include glycerin, mannitol, sorbitol, sodium chloride and other electrolytes, or the like. Among buffering agents that may be used are sodium hydrogen phosphate, sodium dihydrogen phosphate, p-hydroxybenzoic acid ester, boric acid and the like. A preservative such as p-hydroxybenzoic acid ester, benzalkonium chloride, stabilized oxychloro complexes (Purite®), phenylmercuric acetate, chlorobutanol, benzyl alcohol, parabens, thimerosal or the like may be desirably added. A stabilizer such as an edetate salt, including edetate disodium, edetate calcium disodium, edetate sodium, edetate trisodium, and edetate dipotassium sodium edetate or the like may also be used. Further, it may be desirable to enhance the viscosity of an ophthalmic solution by addition of polyvinyl alcohol, polyvinyl pyrrolidone, polyacrylic acid, cellulosic ethers (e.g., hydroxypropyl methyl cellulose hydroxyethyl cellulose, ethyl hydroxyethyl cellulose, hydroxypropyl cellulose, methyl cellulose, and carboxymethyl cellulose, carbomers, polyvinyl alcohol, polyvinyl pyrrolidone, alginates, carrageenans, guar, karaya, agarose, locust bean, xanthan gums or the like. The pH of the ophthalmic solution may be adjusted with sodium hydroxide, hydrochloric acid or the like to a suitable pH, generally between about 6.8 and 7.6. The formulations containing olopatadine may also contain other active agents.

Ophthalmic formulations typically are applied to the eyes from once to a few times a day in an amount of one to several drops at a time, though in more severe cases the drops may be applied several times a day.

Pharmaceutical compositions of this invention may contain inert pharmaceutically acceptable carriers, which may be solids or liquids, in addition to an effective amount of the olopatadine salt as the active ingredient providing anti-allergic activity. Among the solid form compositions are powders, capsules, tablets, granules, cachets and suppositories. Solid pharmaceutically acceptable carriers include diluents, flavoring agents, solubilizers, lubricants, suspending agents, binders, tablet disintegration agents or encapsulating material. In tablets, the active compound is mixed with an appropriate amount of carrier having the required binding properties and the mixture is compacted into tablet form. The carrier for powders is finely divided solid which is admixed with the finely divided olopatadine or a salt thereof. The solid compositions preferably contain from about 2% to about 30% olopatadine or pharmaceutically acceptable salt thereof. Suitable solid carriers for such compositions and the methods for making such composition are well known in the art.

In yet another aspect, a novel and nonobvious crystalline form of olopatadine hydrochloride, referred to herein as olopatadine hydrochloride Form B, has been discovered. Olopatadine hydrochloride Form B is characterized as having substantially the following X-ray diffraction peaks (degrees two-theta) obtained using copper K alpha radiation: 9.03, 10.39, 16.93, 20.09, 21.90, 22.94, 23.23, and 29.82.

Olopatadine hydrochloride is prepared by crystallization or recrystallization from a mixed organic solvent which is a two-phase solvent mixture consisting of an alcohol and an organic solvent which is immiscible or incomplete miscible with the alcohol. The crystallization or recrystallization may be carried out for example by combining an alcoholic solution of olopatadine hydrochloride with the solvent that is immiscible or incompletely miscible with the alcohol. Such crystallization solvents may comprise an alcohol that is (i) methanol or ethanol, preferably methanol, and a $C_6$-$C_{10}$ aliphatic or an cycloaliphatic hydrocarbon, preferably hexane or heptane. Preferably the mixed solvent for crystallization/recrystallization contains between about 40-90% of at least one higher alkane, with the remaining 10-60% of the mixed solvent being at least one lower alkanol. It may be desirable to cool the $C_6$-$C_{10}$ aliphatic or an cycloaliphatic hydrocarbon, e.g., to 0° C.-5° C., before combining it with the alcoholic solution of olopatadine hydrochloride. Crystalline olopatadine hydrochloride Form B preferably has a polymorphic purity of at least 50%, more preferably at least 80%, still more preferably at least 90% and most preferably a polymorphic purity of 95% or greater.

Table 2 below shows the X-ray diffraction data of crystalline olopatadine hydrochloride Form B.

TABLE 2

XRD data of the polymorphic form B of Olopatadine-HCl

| Pos. [°2Th.] | Height [cts] | d-spacing [Å] | Rel. Int. [%] |
|---|---|---|---|
| 9.0322 | 218.87 | 9.79104 | 4.74 |
| 10.3928 | 422.18 | 8.51206 | 9.15 |
| 11.7632 | 55.53 | 7.52333 | 1.20 |
| 12.8876 | 883.52 | 6.86933 | 19.15 |
| 13.1754 | 661.73 | 6.71993 | 14.34 |
| 13.7171 | 246.85 | 6.45575 | 5.35 |
| 14.7647 | 1661.61 | 5.99995 | 36.02 |
| 15.1360 | 146.07 | 5.85363 | 3.17 |
| 15.8005 | 328.49 | 5.60888 | 7.12 |
| 16.5225 | 725.16 | 5.36540 | 15.72 |
| 16.9308 | 453.07 | 5.23693 | 9.82 |
| 17.7290 | 1187.40 | 5.00290 | 25.74 |
| 18.1839 | 1546.70 | 4.87874 | 33.53 |
| 18.4794 | 3368.00 | 4.80140 | 73.01 |
| 19.1585 | 2841.52 | 4.63270 | 61.60 |
| 19.4029 | 4613.04 | 4.57491 | 100.00 |
| 20.0877 | 399.38 | 4.42047 | 8.66 |
| 20.9111 | 2386.00 | 4.24822 | 51.72 |
| 21.5036 | 79.21 | 4.13249 | 1.72 |
| 21.9018 | 622.74 | 4.05826 | 13.50 |
| 22.5258 | 658.40 | 3.94722 | 14.27 |
| 22.9371 | 2095.19 | 3.87737 | 45.42 |
| 23.2339 | 941.91 | 3.82850 | 20.42 |
| 23.7351 | 719.65 | 3.74878 | 15.60 |
| 24.3828 | 330.26 | 3.65065 | 7.16 |
| 24.8627 | 775.84 | 3.58126 | 16.82 |
| 25.1064 | 920.85 | 3.54704 | 19.96 |
| 25.6471 | 2087.97 | 3.47349 | 45.26 |
| 26.4009 | 1147.08 | 3.37599 | 24.87 |
| 26.6609 | 487.98 | 3.34366 | 10.58 |
| 27.1758 | 209.98 | 3.28147 | 4.55 |
| 27.4220 | 231.63 | 3.25256 | 5.02 |
| 27.6952 | 147.71 | 3.22110 | 3.20 |
| 27.9992 | 100.21 | 3.18681 | 2.17 |
| 28.7138 | 4028.32 | 3.10910 | 87.32 |
| 29.0760 | 407.48 | 3.07119 | 8.83 |
| 29.8165 | 1780.53 | 2.99659 | 38.60 |
| 30.6454 | 315.36 | 2.91740 | 6.84 |
| 31.0433 | 255.98 | 2.88091 | 5.55 |
| 31.5967 | 921.52 | 2.83170 | 19.98 |
| 31.9080 | 181.87 | 2.80477 | 3.94 |
| 32.2776 | 166.68 | 2.77350 | 3.61 |
| 32.7139 | 240.25 | 2.73750 | 5.21 |
| 33.4546 | 58.38 | 2.67857 | 1.27 |
| 33.9239 | 334.39 | 2.64258 | 7.25 |
| 34.1663 | 343.06 | 2.62438 | 7.44 |
| 35.0217 | 124.44 | 2.56222 | 2.70 |
| 35.9210 | 323.30 | 2.50011 | 7.01 |
| 36.1062 | 453.62 | 2.48771 | 9.83 |
| 36.3100 | 293.74 | 2.47421 | 6.37 |
| 37.3211 | 381.86 | 2.40948 | 8.28 |
| 37.5342 | 273.62 | 2.39628 | 5.93 |
| 38.2810 | 78.59 | 2.35124 | 1.70 |
| 38.6809 | 114.43 | 2.32784 | 2.48 |
| 39.4286 | 598.54 | 2.28541 | 12.97 |

Form A is characterized by the XRD data shown in Table 3 below. Synchrotron, as well as X-ray measurements, of a single crystal confirm this form clearly.

TABLE 3

XRD data of the polymorphic form A of Olopatadine-HCl

| Pos. [°2Th.] | Height [cts] | d-spacing [Å] | Rel. Int. [%] |
|---|---|---|---|
| 6.3430 | 130.21 | 13.93480 | 1.90 |
| 9.6079 | 22.52 | 9.20564 | 0.33 |
| 11.1401 | 368.41 | 7.94268 | 5.37 |
| 12.7051 | 1486.69 | 6.96759 | 21.69 |
| 13.1893 | 79.77 | 6.71291 | 1.16 |
| 13.7770 | 235.08 | 6.42781 | 3.43 |
| 14.2596 | 195.87 | 6.21136 | 2.86 |
| 14.6097 | 240.91 | 6.06330 | 3.51 |
| 15.5027 | 725.52 | 5.71595 | 10.58 |
| 16.5486 | 181.46 | 5.35699 | 2.65 |
| 17.6679 | 1517.55 | 5.02005 | 22.14 |
| 18.3451 | 1014.50 | 4.83624 | 14.80 |
| 19.0932 | 6855.61 | 4.64842 | 100.00 |
| 19.4339 | 2363.43 | 4.56767 | 34.47 |
| 20.6806 | 1211.49 | 4.29505 | 17.67 |
| 21.6071 | 521.03 | 4.11292 | 7.60 |
| 22.7006 | 1063.61 | 3.91723 | 15.51 |
| 23.8859 | 2119.65 | 3.72546 | 30.92 |
| 24.1082 | 2089.24 | 3.69160 | 30.47 |
| 25.4223 | 1141.80 | 3.50368 | 16.65 |
| 26.5338 | 269.71 | 3.35939 | 3.93 |
| 27.1530 | 1856.18 | 3.28417 | 27.08 |
| 27.6554 | 475.43 | 3.22564 | 6.93 |
| 28.3649 | 2874.05 | 3.14654 | 41.92 |
| 29.3962 | 304.21 | 3.03847 | 4.44 |
| 30.2584 | 806.75 | 2.95382 | 11.77 |
| 31.5538 | 866.28 | 2.83545 | 12.64 |
| 33.7710 | 157.13 | 2.65419 | 2.29 |
| 34.3855 | 122.44 | 2.60816 | 1.79 |
| 34.8219 | 210.14 | 2.57646 | 3.07 |
| 36.0927 | 154.66 | 2.48861 | 2.26 |
| 36.6037 | 107.96 | 2.45503 | 1.57 |
| 37.0480 | 95.14 | 2.42660 | 1.39 |
| 38.4167 | 448.89 | 2.34325 | 6.55 |
| 38.6910 | 495.51 | 2.32726 | 7.23 |

Oshima, E., *J. Med. Chem.*, 1992, 35, 2074-2084 discloses crystallizing olopatadine hydrochloride from acetone/water. Crystallization experiments revealed that Form A, but not Form B, crystallized from a wide range of crystallization solvents, including an acetone/water crystallization solvent.

A. Recrystallization from Ethanol

A suspension of Olopatadine-HCl (1.5 g) in ethanol (80 ml) was heated to reflux to give a clear solution. After cooling to 20-25° C., the suspension was filtered and the wet product was dried under vacuum (14 h, 60° C.) to obtain Olopatadine-HCl (yield: 1.10 g, 73.3%) in the polymorphic form A.

B. Recrystallization from Acetone/Water

A suspension of Olopatadine-HCl (5 g) in acetone (20 ml) was heated to reflux. Then, water (5.6 ml) was added to give a clear solution. After cooling to 20-25° C. first, and then to 0-5° C., the suspension was filtered and the wet product washed with acetone (6 ml) and dried under vacuum (over night, 60° C.) to obtain Olopatadine-HCl (yield: 3.47 g, 69.4%) in the polymorphic form A.

C. Precipitation by Addition of Methanolic Olopatadine-HCl Solution to MTBE

Olopatadine-HCl (1.0 g) was dissolved methanol (in 25 ml) at 30-40° C. and this solution was added to precooled (0-5° C.) MTBE (100 ml). The suspension was filtered and the wet product dried under vacuum (1.5 h, 60° C.) to obtain Olopatadine-HCl (yield: 0.82 g, 82%) in the polymorphic form A.

D. Precipitation by Addition of Olopatadine-HCl DMF Solution to Diisopropylether A solution of Olopatadine-HCl (1.0 g) in DMF (30 ml) was added at 20-25° C. to diisopropylether (100 ml). After one hour stirring at this temperature, the suspension was filtered and the wet product washed with diisopropylether (2-3 ml) and dried under vacuum (over night, 60° C.) to obtain Olopatadine-HCl (yield: 0.9 g, 90%) in the polymorphic form A.

E. Precipitation by Addition of Olopatadine-HCl DMSO Solution to Toluene

A solution of Olopatadine-HCl (1.0 g) in DMSO (7 ml) was added at 20-25° C. to toluene (100 ml). After 40 minutes stirring at this temperature, the suspension was filtered and the wet product was dried under vacuum (overnight, 60° C.) to obtain Olopatadine-HCl (yield: 0.92 g, 92%) in the polymorphic form A.

F. Precipitation by Addition of Methanolic Olopatadine-HCl Solution to Hexane

Olopatadine-HCl (1.0 g) was dissolved in methanol (25 ml) at 35-40° C., and this solution was added to precooled (0-5° C.) hexane (100 ml). The suspension was stirred for 1.5-2 hours at 0-5 then filtered and the wet product dried under vacuum (1.5 h, 60° C.) to obtain Olopatadine-HCl (yield: 0.59 g, 59%) in the polymorphic form B.

G. Precipitation by Addition of Methanolic Olopatadine-HCl Solution to Heptane

Olopatadine-HCl (1.0 g) was dissolved in methanol (25 ml) at 35-40° C., and this solution was added to precooled (0-5° C.) heptane (100 ml). The suspension was stirred for 1.5 hours at 0-5 then filtered and the wet product dried under vacuum (1.5 h, 60° C.) to obtain Olopatadine-HCl (yield: 0.51 g, 51%) in the polymorphic form B.

Olopatadine hydrochloride Form B is characterized by the XRD data shown in Table 4 below.

TABLE 4

Table 4 below shows various results achieved (such as % yield) when differet batches of Form A or Form B of olopatadine-HCl was produced under various conditions.

| | Batch-no. | | | | | |
|---|---|---|---|---|---|---|
| | FE002.01.1.2 | FE002.01.2.2 | FE002.01.2.3 | FE002.01.3.2 | FE002.01.4.2 | FE002.01.5.2 |
| Starting material | 765.63.12 1.5 g | 765.63.12 1.5 g | ML from FE002.01.2.2 | 765.63.12 1.5 g | 765.63.12 1.0 g | 765.63.12 1.0 g |
| Solvent(s) | EtOH abs. | MEK | MEK | EtOAc | THF | Toluene |
| ml | 80 | 130 | 130 | 130 | 100 | 100 |
| Conditions | recrystallization 78° C. → 25° C., 0.5 hr 25° C. | slurry: 78° C., 2 h 40' | crystallization: 78° C. → 25° C., 1.5 h | slurry: 78° C., 3 h | slurry: 65° C., 3.25 h | slurry: 109° C., 2 h 10' |
| Yield [%] | 73.0 | 88.0 | 9.0 | 93.0 | 94.0 | 58.0 |

TABLE 4-continued

Table 4 below shows various results achieved (such as % yield) when differet batches
of Form A or Form B of olopatadine-HCl was produced under various conditions.

| | | | | | | |
|---|---|---|---|---|---|---|
| HPLC-purity [%] | 99.95 | 100.00 | 100.00 | 99.97 | 99.98 | 99.97 |
| further Analytics | | | | | | |
| Polymorphic form | A | A | A | A | A | A |
| Remarks | — | hot filtration | 2. crop from ML FE002.01.2.2 | hot filtration | hot filtration | hot filtration |

| | Batch-no. | | | | | |
|---|---|---|---|---|---|---|
| | FE002.01.5.3 | FE002.01.6.2 | FE002.04.1.2 | FE002.04.2.2 | FE002.04.2.3 | FE002.04.3.2 |
| Starting material | ML from FE002.01.5.2 | 765.63.12 1.0 g | 765.63.12 1.0 g | 765.63.12 1.0 g | ML from FE002.04.2.2 | 765.63.12 1.0 g |
| Solvent(s) | Toluene | MTBE | 1,2-DME | Acetonitrile | Acetonitrile | $CH_2Cl_2$ |
| ml | 100 | 100 | 100 | 100 | 100 | 100 |
| Conditions | crystallization: 109° C. → 25° C., over night | slurry: 55° C., 2.5 h | slurry: 86° C., 2 h | slurry: 81° C., 2 h 10' | crystallization: 81° C. → 25° C., over night | slurry: 38° C., 2.5 h |
| Yield [%] | 35.0 | 95.0 | 87.0 | 68.0 | 18.0 | 91.0 |
| HPLC-purity [%] | 100.00 | 99.98 | 100.00 | 100.00 | 100.00 | 99.98 |
| further Analytics | | | | | | |
| Polymorphic form | A | A | A | A | A | A |
| Remarks | 2. crop from ML FE002.01.5.2 | hot filtration | hot filtration | hot filtration | 2. crop from ML FE002.04.2.2 | hot filtration |

| | Batch-no. | | | | | |
|---|---|---|---|---|---|---|
| | FE002.04.4.2 | FE002.04.5.2 | FE002.04.6.2 | FE002.07.1.2 | FE002.07.1.4 | FE002.07.2.2 |
| Starting material | 765.63.12 1.0 g | 765.63.12 1.0 g | 765.63.12 1.0 g | 765.63.12 1.0 g | ML from FE002.07.1.2 | 765.63.12 1.0 g |
| Solvent(s) | α,α,α-Trifluoro-toluene | DMF/MTBE | Cyclohexane | DMF/EtOAc | DMF/EtOAc | DMF/MIK |
| ml | 100 | 30/100 | 100 | 30/100 | 30/100 | 30/100 |
| Conditions | slurry: 101° C., 3.0 h | precipitation: 20-25° C. | slurry: 79° C., 3 h 10' | precipitation: 20-25° C. | crystallization: 20-25° C. over night | precipitation: 20-25° C. |
| Yield [%] | 94.0 | 87.0 | 99.0 | 9.0 | 76.0 | 38.0 |
| HPLC-purity [%] | 100.00 | 100.00 | 100.00 | 100.00 | 100.00 | 100.00 |
| further Analytics | | | | | | |
| Polymorphic form | A | A | A | A | A | A |
| Remarks | hot filtration | Addition of a DMF solution to MTBE | hot filtration | — | 2. crop from ML FE002.07.1.2 | — |

| | Batch-no. | | | | | |
|---|---|---|---|---|---|---|
| | FE002.07.2.4 | FE002.07.3.2 | FE002.27.1.1 | FE002.29.1.1 | FE002.29.2.1 | FE002.30.1.1 |
| Starting material | ML from FE002.07.2.2 | 765.63.12 1.0 g | 765.63.12 1.0 g | FE002.17.45 1.0 g | FE002.17.45 1.0 g | FE002.17.45 1.0 g |
| Solvent(s) | DMF/MIK | DMF/Diisopropyl-ether | DMSO/Hexafluoro-benzene | DMSO/Isopropanol | DMSO/Acetone | DMSO/Toluene |
| ml | 30/100 | 30/100 | 6.8/22.5 | 7/50 | 7/50 | 7/100 |
| Conditions | crystallization: 0-5° C. over night | precipitation: 20-25° C. | precipitation: 20-25° C. | precipitation: 20-25° C. | precipitation: 20-25° C. | precipitation: 20-25° C. |
| Yield [%] | 50.0 | 90.0 | 90.0 | 67.0 | 83.0 | 89.0 |
| HPLC-purity [%] | 100.00 | 100.00 | 100.0 | 100.00 | 100.00 | 100.0 |
| further Analytics | | | | | | |
| Polymorphic form | A | A | A | A | A | A |
| Remarks | 2. crop from ML FE002.07.2.2 | — | — | — | — | — |

TABLE 4-continued

Table 4 below shows various results achieved (such as % yield) when differet batches of Form A or Form B of olopatadine-HCl was produced under various conditions.

| | Batch-no. | | | | | |
|---|---|---|---|---|---|---|
| | FE002.30.2.1 | FE002.30.3.1 | FE002.32.1.1 | FE002.32.2 | FE002.32.3.1 | FE002.32.4.1 |
| Starting material | FE002.17.45 1.0 g | FE002.17.45 1.0 g | FE002.17.45 1.0 g | FE002.17.45 1.0 g | FE002.17.45 1.0 g | FE002.17.45 1.0 g |
| Solvent(s) | DMSO/Toluene | DMSO/CH$_2$Cl$_2$ | Hexafluorbenzene | water | DMSO/Fluorbenzene | DMSO/MTBE |
| ml | 7/100 | 7/100 | 25 | 10 | 7/100 | 7/100 |
| Conditions | precipitation: 20-25° C. | precipitation: 20-25° C. | slurry: 80° C., 2.5 h | recrystallization: | precipitation: 0-5° C. | precipitation: 0-5° C. |
| Yield [%] | 92.0 | 55.0 | 93.0 | — | 88.0 | 72.0 |
| HPLC-purity [%] | 100.00 | 100.00 | 100.0 | — | 100.00 | 100.00 |
| further Analytics | | | | | | |
| Polymorphic form | A | A Strong texture effect | A | — | A | A |
| Remarks | — | Slow crystallization over night at 20-25° C. | hot filtration | No crystallization | difficultly filterable | difficultly filterable |

| | Batch-no. | | | | | |
|---|---|---|---|---|---|---|
| | FE002.28.3 | FE002.34.1 | FE002.34.2.1 | FE002.34.3.1 | FE002.34.4 | FE002.34.5.1 |
| Starting material | FE002.17.45 5.0 g | FE002.17.45 1.0 g | FE002.17.45 1.0 g | FE002.17.45 1.0 g | FE002.17.45 1.0 g | FE002.17.45 1.0 g |
| Solvent(s) | Acetone/H$_2$O | MeOH/CHCl$_3$ | MeOH/Diisopropylether | MeOH/Hexane | MeOH/Toluene | MeOH/MTBE |
| ml | 20/5.6 | 25/100 | 25/100 | 25/100 | 25/100 | 25/100 |
| Conditions | recrystallization: 58° C. → 0-5° C., 2 h | precipitation: 0-5° C. | precipitation: 0-5° C. | precipitation: 0-5° C. | precipitation: 0-5° C., 1 h −20--−15° C., 1 h | precipitation: 0-5° C. |
| Yield [%] | 69.4 | — | 86.0 | 59.0 | — | 82.0 |
| HPLC-purity [%] | 99.99 | — | 100.00 | 100.00 | — | 100.00 |
| further Analytics | | | | H$_2$O: 0.20%, MeOH: 0.082%, Hexane: 0.092%, FT-IR, DSC | | |
| Polymorphic form | A | — | A | B | — | A |
| Remarks | — | No crystallization | Moderately filterable | Crystallization after 10-20 min. → 2 phase suspension | No crystallization | Moderately filterable |

| | Batch-no. | | | | | |
|---|---|---|---|---|---|---|
| | FE002.34.6.1 | FE002.34.7.1 | FE002.34.8.1 | FE002.34.9.1 | FE002.34.10.1 | FE002.40.1 |
| Starting material | FE002.17.45 1.0 g | FE002.17.45 1.0 g | FE002.17.45 1.0 g | FE002.17.45 1.0 g | FE002.17.45 1.0 g | FE002.17.45 2.0 g |
| Solvent(s) | MeOH/AcOEt | MeOH/Hexafluorbenzene | MeOH/MIK | MeOH/BuOH | H$_2$O | MeOH/Hexane |
| ml | 25/100 | 25/50 | 25/100 | 25/100 | 10 | 50/200 |
| Conditions | precipitation: 0-5° C. | precipitation: 0-5° C. | precipitation: 0-5° C. | precipitation: 0-5° C. | precipitation: | precipitation: 0-5° C. |
| Yield [%] | 66.0 | 68.0 | 70.0 | 68.0 | 97.0 | 63.5 |
| HPLC-purity [%] | 100.00 | 100.00 | 100.00 | 100.00 | 100.00 | 100.00 |
| further Analytics | | | | | | H$_2$O: 0.17%, MeOH: 0.13%, Hexane: 0.022%, FT-IR, DSC |
| Polymorphic form | A | A | A | A | (A) only partial crystalline, bad resolution in XRD | B |
| Remarks | Freely filterable | — | Freely filterable | Crystallization after 30 min, suspension difficultly filterable | Solution slowly concentrated until crystalllization started | reproduction of FE002.34.3.1 |

TABLE 4-continued

Table 4 below shows various results achieved (such as % yield) when differet batches
of Form A or Form B of olopatadine-HCl was produced under various conditions.

| | | Batch-no. | | |
|---|---|---|---|---|
| | | FE002.43.1 | FE002.45.1.1 | FE002.45.1.2 |
| | Starting material | FE002.17.45 1.0 g | FE002.17.45 1.0 g | FE002.17.45 1.0 g |
| | Solvent(s) ml | Water/Hexane$^a$/THF$^b$/MeOH$^c$ 10/100/20/20 | MeOH/Heptane 25/100 | MeOH/Dibutylether 25/100 |
| | Conditions | precipitation: 0-5° C. | precipitation: 0-5° C. | precipitation: 0-5° C. |
| | Yield [%] | — | 51.0 | 92.0 |
| | HPLC-purity [%] | — | 100.00 | 100.00 |
| | further Analytics | | | |
| | Polymorphic form | — | B | A |
| | Remarks | No crystallization | Crystallization after 10-15 min. → 2 phase suspension | Moderately filterable |

Figure 2:
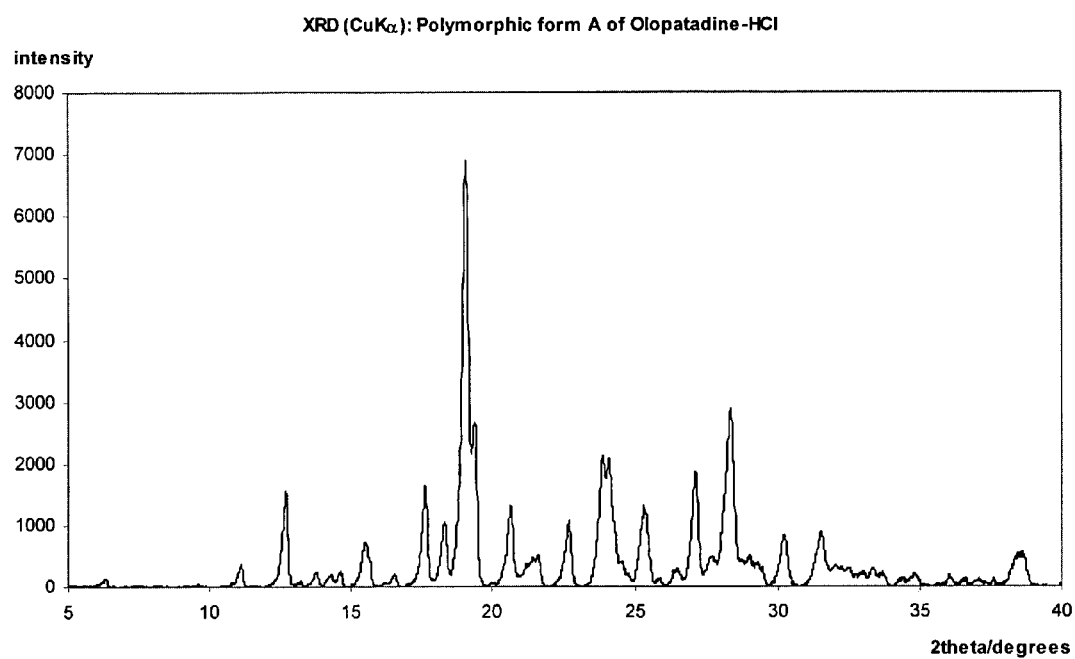
FIG. 2 is an XRD profile of the polymorphic Form A of Olopatadine-HCl.

The X-ray powder diffraction pattern shown in FIG. 1 is that of olopatadine hydrochloride Form B (Batch FE002.34.3.1). The X-ray powder diffraction pattern shown in FIG. 2 is that of olopatadine hydrochloride Form A (Batch 765.63.12). The intensities of the various XRD peaks demonstrated in FIG. 1 and FIG. 2 may vary due to texture effects, as known in the art.

Throughout this document, various books, patents, journal articles, web sites and other publications have been cited. The entireties of each of these books, patents, journal articles, web sites and other publications are hereby incorporated by reference herein.

EXAMPLES

The following examples describe and illustrate polymorphs of olopatadine-HCl, and methods within the present invention, and are intended to be merely illustrative of the present invention, and not limiting thereof in either scope or spirit. Those of skill in the art will readily understand that variations of certain of the conditions and/or steps employed in the procedures described in the examples can be used to prepare these polymorphs, olopatadine or salts thereof. All yields that have been calculated were corrected by assay.

Example 1

Synthesis of the Intermediate
4-(2-Carboxybenzyloxy)Phenylacetic Acid
(Olo-IM1)

A solution of 4-hydroxyphenylacetic acid (90.0 g, 0.58 mol; assay >98%) and phthalide (85.07 g, 0.63 mol) in DMF (323 g) was heated to an internal temperature of 130° C. The pressure was reduced to 800 mbar and sodium methoxide (224.6 g, 1.25 mol, assay: 30% methanolic solution) was added slowly to the mixture maintaining the internal temperature above 100° C. During the addition methanol was distilled off, and after the addition the distillation was continued under normal pressure until the internal temperature increased to 130° C. again (260 g distillate). After stirring at this temperature for 6.5 h, phthalide (8.5 g, 0.06 mol) was added and the mixture was stirred overnight (16 h). Afterwards the mixture was cooled to 100° C. and hydrolyzed with water (1040 g). After cooling to <10° C., the pH of the mixture was adjusted to pH 1 with hydrochloric acid (163.5 g, 1.43 mol; assay: 32%). The product was filtered off, washed with water (700 g) and dried under vacuum for 15 hours at 60° C. to give crude 4-(2-carboxybenzyloxy)phenylacetic acid (Olo-IM1) (yield: 174.6 g, 0.48 mol, 82.1%; HPLC assay: 78.0%).

The crude Olo-IM1 (50.0 g, assay: 78.0%, 0.14 mol) was recrystallized from acetonitrile/water (40 ml, 1/1). After filtration, the wet product washed successively with acetonitrile/water (98 ml, 1/1) and water (20 ml) to give slightly orange colored 4-(2-carboxybenzyloxy)phenylacetic acid (Olo-IM1) (yield: 35.27 g, 0.12 mol, 88.1%; HPLC assay: 97.4%; overall yield: 72.3%).

Example 2

Synthesis of the Intermediate
6,11-dihydro-11-oxo-dibenz[b,e]oxepin-2-acetic acid
(Olo-IM2)

To a suspension of 4-(2-carboxybenzyloxy)phenylacetic acid (Olo-IM1) (300.09 g, 1.04 mol; assay: 99.0%) and trifluoromethane sulfonic acid (4.77 g, 0.03 mol; assay: 98.0%) in toluene (1122 g) was added slowly trifluoroacetic anhydride (255.18 g, 1.20 mol; assay: 99.0%) at 20-35° C. The brown solution was stirred after complete addition of trifluoroacetic anhydride for 1 hour at 20-25° C. and the mixture was then hydrolyzed with water (99.0 g). Afterwards, the mixture was distilled under normal pressure until the steam temperature was 105-110° C. (1191 g two-phase distillate). The residue was diluted with toluene (261 g) and the suspension was heated to reflux. The dark solution was then cooled to 75° C. and seeded with crystals of 6,11-dihydro-11-oxo-dibenz[b,e]oxepin-2-acetic acid (Olo-IM2). The suspension was stirred after cooling to 20-25° C. for additional 1-2 hours at this temperature. The product was filtered off, washed with cyclohexane (600 g) and water (390 g) and dried under vacuum (20 h, 50° C.) to give 6,11-dihydro-11-oxo-dibenz[b,e]oxepin-2-acetic acid (Olo-IM2) (yield: 203.21 g, 0.76 mol, 73.0%; HPLC assay >99.5%, HPLC purity: 99.62%). This product was then recrystallized from a mixture of cyclohexane (700 g) and toluene (1892 g). After filtration the wet product was washed with cyclohexane (466 g) and dried under vacuum (15 h, 70° C.) to give slightly gray colored 6,11-dihydro-11-oxodibenz[b,e]oxepin-2-acetic acid (Olo-IM2) (yield: 198.4 g, 0.74 mol, 97.6%; HPLC assay >99.5%, HPLC purity: 99.90%; overall yield: 71.3%).

Example 3

Synthesis of the Intermediate
3-bromopropyltriphenylphosphonium bromide
(Olo-IM3)

To a stirred solution of triphenylphosphine (511 g, 1.85 mol; assay: 95.0%) in toluene (800 g), 1,3-dibromopropane (371 g, 1.82 mol; assay: 99.0%) was added slowly within 1 hour at <5° C. After complete addition the solution was heated to reflux for 17 hours whereupon a suspension was obtained which was then cooled to room temperature. The product was filtered off at 20° C., washed with toluene (2×800 g) and dried under vacuum (21 h, 60° C.) to give 3-bromopropyltriphenylphosphonium bromide (Olo-IM3) as a white, crystalline solid (yield: 757 g, 1.63 mol, 89.6%).

Example 4

Synthesis of the Wittig Reagent
3-dimethylaminopropyltriphenylphosphonium
Bromide *HBr (Olo-IM4)

To a stirred suspension of 3-bromopropyltriphenylphosphonium bromide (Olo-IM3) (420 g, 0.90 mol) in absolute ethanol (664 g) a solution of dimethylamine in absolute ethanol (368 g, 2.69 mol, assay: 33%) was added slowly within 30 minutes at room temperature. After complete addition the suspension was stirred 1 hour at reflux whereupon a solution was obtained. The solution was cooled to a temperature of 0-10° C. and acetyl bromide (202.7 g, 1.65 mol) was added dropwise until the pH was ≦1, and the resulting suspension was allowed to warm to 20-25° C. After the white suspension was filtered the wet product washed with absolute ethanol (237 g) and then dried under vacuum (15 h, 70° C.) to give 3-dimethylaminopropyltriphenylphosphonium bromide*HBr (Olo-IM4) as a white solid (yield: 471.2 g, 0.77 mol, 85.1%; HPLC assay: 83.2%, HPLC purity: 98.72%).

The crude material (460 g, 0.75 mol; assay: 83.2%) was further purified by suspending it in absolute ethanol (395 g) and stirring at reflux temperature. After addition of further absolute ethanol (435 g) all material was dissolved and the solution was allowed to cool to room temperature, with seeding at 69° C. to initiate crystallization. After 4 hours stirring at room temperature the product was filtered off, washed with ethanol (140 g) and then dried under vacuum (15 h, 70° C.) to give 3-dimethylaminopropyltriphenylphosphonium bromide*HBr (Olo-IM4) as a crystalline white solid (yield: 333.7 g, 0.66 mol, 87.2%; HPLC assay >99.9%, HPLC purity: 99.85%, overall yield: 74.2%).

Example 5

Synthesis of the Wittig Reagent
3-dimethylaminopropyltriphenylphosphonium
Bromide (Olo-IM4, Free Base)

(a) from 3-dimethylaminopropyltriphenylphosphonium bromide*HBr (Olo-IM4)

A flask containing 3-dimethylaminopropyltriphenylphosphonium bromide*HBr (128.1 g, 0.25 mol), $Na_2CO_3$ (31.8 g, 0.30 mol) and 2-propanol (590 g) was stirred at 50° C. for 6 hours. The mixture was then cooled to room temperature, filtered through celite (15 g) and the cake was washed with 2-propanol (2×186 g). Under reduced pressure (45° C., 100 mbar) most of the solvent was removed to obtain a supersaturated product solution (170 g). Under stirring this solution was seeded with Olo-IM4 (free base) crystals to initiate the crystallization. To the white suspension was added MTBE (240 g) and cyclohexane (253 g), and the mixture was stirred overnight for complete crystallization. The product was filtered off, washed with MTBE (2×74 g) and dried under vacuum for 7 hours at 50° C. to give 3-dimethylaminopropyltriphenylphosphonium bromide (Olo-IM4, free base) as a white, crystalline solid (yield: 101.7 g, 0.24 mol, 94.4%).

(b) from 3-bromopropyltriphenylphosphonium bromide (Olo-IM3) with dimethylamine solution To a stirred suspension of 3-bromopropyltriphenylphosphonium bromide (11.64 g, 25.1 mmol) in 2-propanol (78.5 g), a solution of dimethylamine in absolute ethanol (10.25 g, 75.0 mmol; assay: 33%) was added slowly within 10 minutes at room temperature. After complete addition the suspension was stirred for 45 minutes at reflux temperature, then 26.4 g of solvent was distilled off under reduced pressure (62° C., 500 mbar). After addition of $K_2CO_3$ (4.15 g, 30 mmol) the suspension was stirred at reflux temperature for 3.5 hours, then cooled to room temperature, filtered through celite (3 g), and the cake washed with 2-propanol (2×15.7 g). Under reduced pressure (45° C., 100 mbar), most of the solvent was removed to obtain a supersaturated product solution (25.1 g). Under stirring this solution was seeded with Olo-IM4 (free base) crystals to initiate the crystallization. To the white suspension MTBE (37 g) and cyclohexane (39 g) were added slowly and the suspension was overnight for complete crystallization. The product was filtered off, washed with MTBE (2×18.5 g) and dried under vacuum (7 h, 50° C.) to give 3-dimethylaminopropyltriphenylphosphonium bromide (Olo-IM4, free base) as a white, crystalline solid (yield: 7.53 g, 17.1 mmol, 68.0%, HPLC assay: 97.03%).

(c) from 3-bromopropyltriphenylphosphonium bromide with gaseous dimethylamine

Into a stirred suspension of 3-bromopropyltriphenylphosphonium bromide (58.02 g, 125 mmol) in 2-propanol (400 g) gaseous dimethylamine (17.3 g, 383 mmol) was bubbled within 15 minutes at 0-10° C. After that, the suspension was heated to 35-40° C. and stirred for 16 hours.

Then from the clear solution 183 g of solvent was distilled off under reduced pressure (58-61° C., 400 mbar). At 45-50° C., water (3.0 g) and $K_2CO_3$ (17.28 g, 125 mmol) were added. Under reduced pressure (400 mbar), the suspension was heated to 55-60° C. and stirred for 9 hours, during which time some solvent was distilled off and most of the dimethylamine was removed. The amount of the distilled solvent (65 g) was added again. The white suspension was cooled to 20-25° C., and stirred for 30-60 minutes. Then the suspension was filtered and washed with 2-propanol (55 g). The white solid (dry 24.15 g) was discarded. From the filtrate (291 g) a total of 183 g solvent was distilled off at 60-62° C. under reduced pressure (400 mbar). The residue was cooled to 20-25° C. and MTBE (202 g) was added. The white milky emulsion was seeded with Olo-IM4 (free base) crystals to initiate the crystallization. The crystallization proceeded very fast and then the white suspension was heated to reflux (55° C.) and stirred for 1 hour. Then the suspension was cooled to 20-25° C. and stirred for 3 hours. The product was filtered off, washed with MTBE (50 g) and dried under vacuum (12 h, 50° C.) to give 3-dimethylaminopropyltriphenylphosphonium bromide (Olo-IM4, free base) as a white, crystalline solid (yield: 51.34 g, 116 mmol, 92.8%, HPLC purity: 99.17%, HPLC assay: 96.45%).

Example 6

(Z)-11-[3-dimethylaminopropylidene]-6,11-dihydrodibenz[b,e]oxepin-2-acetic Acid Hydrochloride (Olopatadine Hydrochloride)

Procedure 1

Step a: Preparation of Olopatadine Hydrobromide

Under a nitrogen atmosphere a 2500 ml 5-neck flask with a mechanical stirrer was charged with 3-dimethylaminopropyltriphenylphosphonium bromide hydrobromide (Olo-IM4) (299.6 g, 0.584 mol; HPLC assay: 99.4%) and sodium hydride (70.28 g, 1.757 mol, assay: 60%). Precooled (4° C.) dry THF (284 g) was added and the suspension was stirred under $N_2$ atmosphere at 20-30° C. for 40 minutes and at 55-60° C. for 3 hours. After 160 g of the solvent from the orange suspension was distilled off under normal pressure, the reaction mixture was cooled to <10° C. Then a solution of 6,11-dihydro-11-oxo-dibenz[b,e]oxepin-2-acetic acid (Olo-IM2) (57.69 g, 0.215 mol, HPLC assay >99.5%) in dry THF (100 g) was added carefully and the reaction mixture was stirred for 20-30 hours at 20-25° C. The reaction mixture was cooled to <10° C. and a solution of water (25 g) in THF (75 g) was added slowly. After dilution with water (270 g) the two-phase solution was separated and the water layer was concentrated under normal pressure until 286 g distillate was obtained. Prior to concentration of this layer, the pH was checked (at 20-25° C.) to ensure that the pH was not lower than pH 12 (and raised to pH 12 or greater, if necessary, with 30% aqueous NaOH).

The residue was diluted with water (765 g), extracted five times with toluene (500 g each). A solution of 2-methyltetrahydrofuran (490 g) and 2-propanol (90 g) was added and the pH of the water layer was adjusted from 13.8 to 4.3-4.4 by addition of an aqueous hydrobromic acid solution (169.2 g, 1.04 mol; assay: 48%). The phases were separated and the water phase was extracted three times with a mixture of 2-methyltetrahydrofuran (490 g) and 2-propanol (90 g) each. The combined brown organic layers were evaporated under reduced pressure at 500 mbar until a distillate of 2350 g was obtained. The remaining brown oil was diluted with n-butanol (233 g) and the mixture was evaporated again under reduced pressure at 500 mbar to remove water by azeotropic distillation (275 g two-phase distillate). To the residue, n-butanol (537 g) and seeding material were added, and the slurry was stirred at 75° C. for one hour. The slurry was cooled to 20-25° C., stirred at this temperature for 14 hours and filtered off. The wet product washed with n-butanol (130 g) and dried under vacuum (15 h, 80° C.) to give beige powdery Olopatadine Hydrobromide (yield: 52.11 g, 0.122 mol, 56.9%; HPLC assay: 98.17%, HPLC purity: 98.16%, Z/E-Isomers: 98.5/1.5).

In a 750 ml 5-necked flask a suspension of the above-obtained dry product (50.0 g, 0.117 mol; HPLC assay: 98.17%) in n-butanol (325 g) was heated at 80° C. for one hour (water content of the mixture: 1.87%). Then the pale beige slurry was slowly cooled to <5° C. and stirred at this temperature for one hour. After filtration the wet product washed with n-butanol (200 g) and dried under vacuum (15 h, 60° C.) to give pale beige Olopatadine Hydrobromide (yield: 48.22 g, 0.114 mol, 96.95%; HPLC assay: 98.69%, HPLC purity: 98.60%, Z/E-Isomers: 98.9/1.1).

Step b: Conversion of Olopatadine HBr to Olopatadine (Free Base)

In a 350 ml 5-necked flask Olopatadine hydrobromide (44.0 g, 0.104 mol; HPLC assay: 98.69%) was suspended in water (101 g). The suspension was adjusted to a pH in the range of pH 6.8-7.2 at 20-25° C. using 2 N aqueous sodium hydroxide solution (55 g). Seed crystals of olopatadine free base were added to the beige solution, and the mixture was stirred at 20-25° C. for one hour while monitoring the pH (and maintaining a pH of 6.8-7.2 using 2 N aqueous sodium hydroxide solution as necessary). The nearly white slurry was stirred 17 hours at 20-25° C. and for two hours at <5° C. The slurry was then filtered and the wet product washed with water (144 g) and dried under vacuum for 15 hours at 60° C. to give off-white Olopatadine (yield: 38.99 g, 0.101 mol, 97.63%; HPLC assay: 87.70%, HPLC purity: 99.09%, water content: 12%, Z/E-Isomers: 99.4/0.6).

Step c: Conversion of Olopatadine (Free Base) to Olopatadine Hydrochloride

To a suspension of the above obtained Olopatadine (of 30.0 g, 0.078 mol; HPLC assay: 87.70%) in acetone (226 g) was added concentrated hydrochloric acid (9.73 g, 0.085 mol; assay: 32%). After the addition of hydrochloric acid, the suspension became viscous and further acetone (226 g) was added. The mixture was stirred for one hour at 20-25° C., cooled to <5° C., and stirred for an additional hour at this temperature. After filtration, the white solid washed with acetone (96 g) and dried under vacuum for 15 hours at 60° C. to give white fine powdery Olopatadine Hydrochloride (yield: 28.04 g, 0.065 mol; assay: 99.39% (NaOH), HPLC purity: 99.92%, Z/E-Isomers: 99.98/0.02, yield: 95.60%, polymorphic form A). Overall yield for Olopatadine hydrochloride based on Olo-IM2: 51.5%. Calculated volume yield for the synthesis of Olopatadine-HCl: 1.48%

Procedure 2

Step a: Preparation of Olopatadine Hydrobromide

Under a nitrogen atmosphere a 1250 ml 4-neck flask with a mechanical stirrer, reflux condenser and internal thermometer was charged with 3-dimethylaminopropyltriphenylphosphonium bromide (Olo-IM4, free base) (283.23 g, 0.648 mol, assay: 98.0%), sodium hydride (38.40 g, 0.960 mol, assay: 60%) and dry THF (317 g) at an internal temperature of 20-25° C. The white suspension was heated to 55-60° C. for 2.5 hours whereupon the color changed to orange. After 189 g of the solvent was distilled off under normal pressure, the reaction mixture was cooled to 15-20° C. Then a solution of 6,11-dihydro-11-oxo-dibenz[b,e]oxepin-2-acetic acid (Olo-IM2) (64.39 g, 0.240 mol, HPLC assay >99.5%) in dry THF (111 g) was added carefully and the reaction mixture was stirred for 40 hours at 20-25° C. The reaction mixture was cooled to 0-5° C. and a solution of water (24 g) in THF (60 g) was added slowly (at 0-20° C.). After dilution with water (290 g) and stirring for 10-15 minutes at 20-25° C., the two-phase solution was separated and the water layer was concentrated under normal pressure until 276 g distillate was obtained. Prior to concentration of this layer, the pH was checked (at 20-25° C.) to ensure that the pH was not lower than pH 12 (and raised to pH 12 or greater, if necessary, with 30% aqueous NaOH).

The residue was cooled to 25-30° C. and extracted first with toluene/n-butanol (9/1, 300 g) and then three times with toluene/n-butanol (9/1, 240 g for each extraction). During these extractions three layers were obtained, whereupon each time the two aqueous layers were separated and extracted again. Afterwards the aqueous layers were extracted once with toluene (200 g). In this case only two layers were obtained during the extraction. Then, n-butanol (240 g) was added to the aqueous layer and at 0-10° C., the pH was adjusted from 12.59 to 4.2-4.6 by addition of an aqueous hydrobromic acid solution (78.65 g, 0.467 mol; assay: 48%). The mixture was allowed to warm to 20-25° C., and the aqueous layer was separated and extracted again with n-butanol (240.0 g). The combined organic layers were washed with water (120.0 g) and then treated with charcoal (5.0 g). After filtration of the suspension through a celite filter bed (10.0 g) and washing the filter cake with n-butanol (30 g), the combined filtrates were concentrated in vacuum (200 mbar) until the internal temperature rose to 72-75° C. and 330-390 g distillate was obtained. To the resulting suspension was added water (4.27 g) at 65-74° C. and the mixture was cooled within 2-3 hours to an internal temperature of 20-25° C. The suspension was stirred at this temperature for 16 hours and then filtered. The wet product washed with n-butanol (72.0 g) and dried under vacuum for 14 hours at 80° C. to give a beige solid (yield: 54.91 g, 0.128 mol, 53.5%; HPLC assay: 97.85%, HPLC purity: 97.80%, Z/E-Isomers: 98.1/1.9). This product is used for the next step without further purification.

Step b: Conversion of Olopatadine HBr to Olopatadine (Free Base)

A 500 ml 3-neck flask was charged with the olopatadine HBr product provided in step a. (54.91 g, 0.128 mol; HPLC assay: 97.85%). At 20-25° C. a solution of NaOH (5.12 g, 0.128 mol) in water (374 g) was then added, whereupon after 5 minutes a yellow solution was obtained (pH=6.4). To this mixture additional 2 N NaOH (2.46 g, 4.6 mmol) was added to adjust the pH to 6.8-7.2 (the crystallization of olopatadine free base starts normally spontaneously after the neutralization), and olopatadine seed crystals (20 mg) were added. The mixture was stirred at 20-25° C. for one hour under monitoring of the pH (the pH was maintained at pH 6.8-7.2 using 2 N aqueous sodium hydroxide solution as necessary). After stirring 20 hours at 20-25° C., the beige suspension was filtered, the wet product washed with water (103 g) and dried under vacuum for 23 hours at 65° C. to give a beige solid (yield: 42.40 g, 0.123 mol, 96.09%; HPLC assay: 97.71%, HPLC purity: 99.03%, water content: 2.80%, Z/E-Isomers: 99.2/0.8).

Step c: Conversion of Olopatadine (Free Base) to Olopatadine Hydrochloride

To a suspension of the olopatadine (free base) produced in step b. (42.40 g, 0.123 mol; HPLC assay: 97.71%) in acetone (601 g) was added concentrated hydrochloric acid (15.39 g, 0.135 mol; assay: 32%). The white suspension was stirred 15 hours at 20-25° C. After the filtration, the white solid washed with acetone (72.5 g) and dried under vacuum for 14 hours at 60° C. to give an off white powdery olopatadine hydrochloride (yield: 44.35 g, 0.119 mol; assay: 100% (HPLC), HPLC purity: 99.96%, Z/E-Isomers: 99.97/0.03, yield: 96.7%, polymorphic form A). Overall yield for olopatadine hydrochloride based on Olo-IM2: 49.7%. Calculated volume yield for the synthesis of Olopatadine-HCl: 5.0%

Example 7

This example relates to variation of certain parameters involved in the Wittig reaction and work-up procedure described in step (a) of Procedures 1 and 2 of Example 6 to prepare olopatadine hydrobromide (i.e., Wittig reaction conditions; quenching; washing steps; extraction using nBuOH; and charcoal treatment). As shown in the Tables below, the resultant olopatadine product was analyzed for overall yield.

TABLE 5

| Reagents for the Wittig reaction and work up procedure (isolation from the reaction mixture) | Batch 1 | Batch 2 | Batch 3 |
|---|---|---|---|
| Wittig reaction: | | | |
| Olo-IM2 (mmol): | 240 | 240 | 240 |
| NaH (equivs.): | 4.0 | 4.0 | 4.0 |
| Olo-IM4 free base (equivs.): | 2.7 | 2.7 | 2.7 |
| Stirring time and internal temperature for Wittig reaction: | 29.5 hr 20-25° C., 8.5 hr 25-30° C. | 63 h 19-25° C. | 39.25 h 18-25° C. |
| amount of Olo-IM2 (after Wittig reaction, determined by HPLC): | 1.57% | 1.42% | 1.51% |
| Quenching: | | | |
| 1) addition of THF/$H_2O$: | 24 g $H_2O$ + 60 g THF | 24 g $H_2O$ + 60 g THF | 24 g $H_2O$ + 60 g THF |
| 2) further addition of $H_2O$: | 290 g | 290 g | 290 g |
| reaction yield of Olopatadine: | 66.2% | 66.4% | 67.2% |
| ratio Z:E-isomer: | 69.9:30.1 | 69.6:30.4 | 70.6:29.4 |
| Washing Steps: | | | |
| 1) toluene/BuOH 9:1: | 1 × 300 g, 3 × 240 g | 1 × 300 g, 3 × 240 g | 1 × 300 g, 3 × 240 g |
| 2) toluene: | — | 1 × 200 g toluene | 1 × 200 g toluene |
| pH aqueous layer: | 12.86 (9° C.) | 12.80 (10° C.) | 12.59 (22° C.), 12.40 (5° C.) |
| Loss of yield (Z-isomer) in combined organic layers: | 1.9% | 2.1% | 1.8% |
| Extraction of Olopatadine and Olo-BP1 (E isomer): | | | |
| 1) amount of added 48% HBr to adjust the pH: | 81.02 g (481 mmol) | 78.05 g (463 mmol) | 78.65 g (466 mmol) |

TABLE 5-continued

| Reagents for the Wittig reaction and work up procedure (isolation from the reaction mixture) | Batch 1 | Batch 2 | Batch 3 |
|---|---|---|---|
| 2) pH after HBr addition: | 4.32 (23° C.) | 4.28 (20° C.) | 4.20 (22° C.) |
| Amount of n-butanol used for the extraction: | 2 × 240 g | 2 × 240 g | 2 × 240 g |
| Overall yield of Z-isomer (Olo) after extraction in combined organic layers: | 62.4% | 62.4% | 64.7% |
| Water content combined organic layer: | not determined | not determined | 17.72% |
| Loss of yield of olopatadine (Z-isomer) in aqueous layer: | 0.07% | 0.04% | 0.02% |
| Amount of water for washing combined organic layer: | 120.0 g | 120.0 g | 120.0 g |
| Charcoal treatment: | | | |
| amount of charcoal: | 5.0 g | 7.0 g | 5.0 g |
| Conditions: | 2 hr 20-25° C., 30' 30-35° C. | 16 hr 20-25° C., 30' 30-35° C. | 1.5 hr 30-40° C. |
| Amount of nBuOH for washing of the filter cake: | 30.0 g | 30.0 g | 30.0 g |
| Water content of the filtrate: | 15.55% | 18.04% | 18.42% |
| Overall yield of Z-isomer in the filtrate: | 62.4% | 61.5% | 63.7% |

The yields were determined by quantitative HPLC.

The results that are present in Table 5 show the efficiency and robustness of the process for the preparation and isolation of olopatadine HBr from the reaction mixture. Neither a prolonged stirring time of the Wittig reaction (up to 63 h) nor reaction temperatures up to 30° C. had an adverse influence on the yield of the product or the selectivity of the reaction, and isolation of the products as their HBr salts gave high yields (reaction yield of Z-isomer: 66-67% and overall yield of olopatadine (Z-isomer) after extraction with nBuOH: 62-64%).

Example 8

This example relates to crystallization of the olopatadine HBr from the organic layer (n-BuOH) directly after the extraction. The initial water content (see Table 6) was reduced by azeotropric distillation to initiate the crystallization. Fractional crystallization to separate the Z/E-diastereomers as their hydrobromide salts provided olopatadine HBr with high diastereomeric purity. Typical temperatures ranged of from about 20-25° C. and the final water content were typically in the range of from about 1-3%. Lower temperatures (0-5° C.) and/or lower water content gave inferior separation of diastereomers.

The initial organic layer (olopatadine HBr-containing solution) contained 15.5% water after the extraction and had a diastereomer (Z/E) ratio of 70/30. The organic layer was divided into six portions (same size) and the portions 3-6 were diluted with the corresponding amounts of nBuOH first. Then all solutions were concentrated by azeotropic distillation in the same manner (equal amounts of solvent were distilled off until the concentrations were obtained which are mentioned in Table 6) to start the crystallization. The suspensions were stirred at room temperature and afterwards batches 2, 4 and 6 were cooled to 0-5° C. and stirred at this temperature for 2.5 hours.

As shown in Table 6 below, temperature has an essential influence on the separation of the diastereomers (see nos. 2, 4 and 6), whereas the influence of olopatadine concentration within the range of from about 5-12% seems to be less crucial. In contrast to portions 1-4, analogous crystallization experiments from less concentrated mixtures (portions 5 and 6) resulted in less yields. The suspensions stirred at from about 0-5° C. formed a crust in the flask, and the precipitation consisted of an agglutinated solid, which appear to have been caused by the simultaneous precipitation olopatadine HBr along with its corresponding E isomer.

TABLE 6

Influence of Temperatures and Concentrations for the Separation of the Diastereomers from the Organic Layer after the Extraction

| Portion No. | Concentration of Olo-HBr (Z-isomer) [%] | Conditions for the Crystallization | | Ratio of Z/E Diastereomers | HPLC purity [%] | HPLC assay [%] | Yield of Z-Isomer [%] |
|---|---|---|---|---|---|---|---|
| 1 | 11-12 | 1. cooled from<br>2. stirring time | 73° C. –> RT<br>16 hrs. at RT | 97.85/2.15 | 97.86 | 97.27 | 53.3 |
| 2 | 11-12 | 1. cooled from<br>2. stirring time at<br>3. additional stirring time | 73° C. –> RT<br>16 hr RT<br>2.5 hrs. at 0-5° C. C | 90.03/9.97 | 89.41 | 88.34 | 53.2 |
| 3 | 7-8 | 1. cooled from<br>2. stirring time at | 73° C. –> RT<br>2.5 d RT | 98.28/1.72 | 98.28 | 97.95 | 55.1 |

TABLE 6-continued

Influence of Temperatures and Concentrations for the Separation
of the Diastereomers from the Organic Layer after the Extraction

| Portion No. | Concentration of Olo-HBr (Z-isomer) [%] | Conditions for the Crystallization | | Ratio of Z/E Diastereomers | HPLC purity [%] | HPLC assay [%] | Yield of Z-Isomer [%] |
|---|---|---|---|---|---|---|---|
| 4 | 7-8 | 1. cooled from<br>2. stirring time at<br>3. additional stirring time | 73° C. –> RT<br>2.5 d RT<br>2.5 hr at 0-5° C. | 87.03/12.97 | 86.53 | 85.63 | 52.7 |
| 5 | 5-6 | 1. cooled from<br>2. stirring time | 73° C. –> RT<br>16 hrs. at RT | 97.89/2.11 | 97.67 | 96.99 | 48.8 |
| 6 | 5-6 | 1. cooled from<br>2. stirring time<br>3. additional stirring time | 73° C. –> RT<br>16 hr at RT<br>2.5 hrs. at 0-5° C. C | 88.76/11.24 | 87.96 | 86.15 | 46.2 |

Example 9

This example relates to the influence of water content in the diastereomer-containing organic layer on the separation of olopatadine HBr from its corresponding E isomer. In the experiment represented in Table 8 below, the initial organic layer (solution) contained 18.4% water after the extraction and the diastereomer ratio (Z/E) was 70/30. The organic layer was divided into five equally sized portions and all five solutions were concentrated by azeotropic distillation in the same manner to start the crystallization. After the distillation, the concentrations (based on Z-isomer Olo-HBr) for the crystallizations of portions 2-4 have been in the range of 13-16% and the water content was adjusted by addition of the corresponding amount of water. The suspensions were cooled from about 73° C. to room temperature and stirred at room temperature for up to 16 hours.

In the case of portion no. 1, the water content was <<1% after the distillation and the initial concentration has been 18%. During the crystallization, the product agglutinated and was not filterable. This agglutination indicates the simultaneous precipitation of the undesired E isomer. Further addition of n-butanol (to a concentration of 12-13%) and stirring at 74° C. again resulted still in a slightly agglutinated but better filterable precipitation.

The results that are present in Table 7 below indicate that water concentration that is much lower than 1% may cause the simultaneous precipitation of the undesired E-diastereomer. In this case (no. 1), with such a low water content in combination with a slightly higher concentration (18% instead of 13-16%, based on Z-isomer) gave an agglutinated precipitation which was not filterable (compare also the results in Table 5). After dilution to a concentration of about 12%, the precipitated product was more filterable, but the product still contained an agglutinated solid. The analytical determination of the ratio of Z/E-isomers confirmed a higher amount of the E-isomer in this product.

On the other hand, with water concentrations of about 4% or more (compare e.g., portion nos. 3, 4 and 5) the yield of the olopatadine decreases without any further enhancement of the Z/E ratio. Water contents of 15-18% can dissolve the product almost completely.

TABLE 7

Influence of the Water Content for the Separation of the Diastereomers
from the Organic Layer after the Extraction and Concentration

| No | Water content [%] | Conditions for the Crystallization | | ratio Z/E Diastereomers | HPLC purity [%] | HPLC assay [%] | Yield of Z-Isomer [%] |
|---|---|---|---|---|---|---|---|
| 1 [a)] | <<1.0% | 1. cooled from<br>2. addition of nBuOH and slurried at<br>3. cooling from<br>4. stirring time | 73° C. –> RT<br>74 C.<br><br>74° C. –> RT<br>2.25 hrs. at RT | 94.61/5.39 | 94.61 | 94.60 | 54.4 |
| 2 | 1.0% | 1. cooled from<br>2. stirring time | 73° C. –> RT<br>16 hrs. at RT | 98.40/1.60 | 98.17 | 98.07 | 50.2 |
| 3 | 1-2% | 1. cooled from<br>2. stirring time | 73° C. –> RT<br>16 hrs. at RT | 98.14/1.86 | 97.76 | 97.41 | 50.4 |
| 4 | 3.0% | 1. cooled from<br>2. stirring time | 73° C. –> RT<br>16 hrs. at RT | 98.40/1.60 | 98.09 | 98.07 | 51.3 |
| 5 | 4.0% | 1. cooled from<br>2. stirring time | 73° C. –> RT<br>16 hrs. at RT | 98.40/1.60 | 98.13 | 97.79 | 47.9 |

Example 10

This example relates to further enrichment of olopatadine hydrobromide that may be obtained by slurrying a diastereomeric mixture containing olopatadine hydrobromide in nBuOH containing small amounts of water. In contrast to the crystallization of Olo-HBr from a mixture of Z/E-isomer with a 70/30 ratio, it could be shown that up to 14% of the Z-isomer can be separated efficiently by slurrying in n-BuOH containing water amounts down to 0.2% (For typical conditions, see Table 8).

TABLE 8

Slurry of enriched Z-isomer Olo-HBr (initial ratio of Z/E isomers: 86/14, concentration 9-10%, based on Z-isomer)

| No | Water content [%] | Conditions for the Slurry | | ratio Z/E Diastereomer | HPLC purity [%] | HPLC assay [%] | Yield of Z-Isomer [%] |
|---|---|---|---|---|---|---|---|
| 1 | 0.2% | 1. slurried<br>2. cooled from<br>3. stirring time at RT | 1 h at 80° C.<br>80° C. -> RT<br>over night | 98.7/1.3 | 98.66 | 95.20 | 94.7 |
| 2 | 1.2% | 1. slurried<br>2. cooled from<br>3. stirring time at RT | 1 h at 80° C.<br>80° C. -> RT<br>over night | 99.2/0.8 | 99.20 | 98.70 | 89.3 |
| 3 | 2.2% | 1. slurried<br>2. cooled from<br>3. stirring time at RT | 1 h at 80° C.<br>80° C. -> RT<br>over night | 99.2/0.8 | 99.20 | 97.80 | 92.6 |

Example 11

This example relates to conversion of olopatadine hydrobromide to olopatadine (free base) with a simultaneous enrichment in the amount of olopatadine relative to its corresponding E isomer. Diastereomeric mixtures containing from 90/10 to 97.5/2.5 ratios of (Z)/(E) isomers were dissolved in an aqueous solution having a pH of between 6.8 and 7.2, and stirred at room temperature for 16 hours, whereby the diastereomeric ratio (Z)/(E) increased substantially.

TABLE 9

Liberation of olopatadine free base from Olopatadine HBr in water at pH = 6.8-7.2

| no | starting material Z/E ratio | Conditions after adjusting the pH = 6.8-7.2 | | ratio of the product isomers Z/E | HPLC purity [%] | Yield of Z-Isomer [%] |
|---|---|---|---|---|---|---|
| 1 | 90/10 | stirring time | 16 hrs. at 20-25° C. | 98.10/1.90 | 98.09 | 92.3 |
| 2 | 95/5 | stirring time | 16 hrs. at 20-25° C. | 98.75/1.25 | 98.54 | 94.3 |
| 3 | 97.5/2.5 | stirring time | 16 hrs. at 20-25° C. | 99.18/0.82 | 99.18 | 92.7 |

Example 12

This example relates to the formation of olopatadine HCl from olopatadine (free base). Addition of hydrochloric acid (assay 32%) to a suspension of olopatadine in acetone. Table 10 below shows various results achieved when starting material containing different ratios of (Z)/(E) isomers are employed. Table 11 shows the results achieved when from 1 to 3 equivalents of the HCl are used to convert olopatadine (free base) to olopatadine hydrochloride. And, Table 12 shows the influence of temperature on the conversion to olopatadine hydrochloride.

TABLE 10

Starting material containing different amounts of the E-isomer

| no | starting material Z/E ratio | Eq. HCl | Conditions | | Ratio of the product isomers Z/E | HPLC purity [%] | Yield of Z-Isomer [%] |
|---|---|---|---|---|---|---|---|
| 1 | 97.6/2.4 | 1.0 | stirring time | 22 hrs. at 20-25° C. | 99.94/0.06 | 99.93 | 88.1 |
| 2 | 98.1/1.9 | 1.0 | stirring time | 16 hrs. at 20-25° C. | 99.95/0.05 | 99.91 | 95.8 |
| 3 | 98.75/1.25 | 1.0 | stirring time | 16 hrs. at 20-25° C. | 99.87/0.13 | 99.82 | 90.1 |
| 4 | 99.2/0.8 | 1.0 | stirring time | 16 hrs. at 20-25° C. | 99.97/0.03 | 99.91 | 98.2 |

TABLE 11

Influence of equivalents of HCl

| no | starting material Z/E ratio | Eq. HCl | Conditions | | ratio of the product isomers Z/E | HPLC purity [%] | Yield of Z-Isomer [%] |
|---|---|---|---|---|---|---|---|
| 1 | 97.6/2.4 | 1.0 | stirring time | 22 hrs. at 20-25° C. | 99.94/0.06 | 99.93 | 88.1 |
| 2 | 97.6/2.4 | 2.0 | stirring time | 22 hrs. at 20-25° C. | 99.98/0.02 | 99.98 | 95.1 |
| 3 | 97.6/2.4 | 3.0 | stirring time | 22 hrs. at 20-25° C. | 99.98/0.02 | 99.98 | 92.2 |

TABLE 12

Influence of temperature during HCl salt formation

| no | starting material Z/E ratio | Eq. HCl | Conditions | | ratio of the product isomers Z/E | HPLC purity [%] | Yield of Z-Isomer [%] |
|---|---|---|---|---|---|---|---|
| 1 | 97.6/2.4 | 1.1 | stirring time | 17.5 hrs. at 0-5° C. | 99.93/0.07 | 99.91 | 97.3 |
| 2 | 97.6/2.4 | 1.1 | stirring time | 17.5 hrs. at 20-25° C. | 99.90/0.10 | 99.89 | 96.3 |
| 3 | 97.6/2.4 | 1.1 | stirring time | 17.5 hrs. at 20-25° C. | 99.90/0.10 | 99.88 | 97.8 |
| 4 | 97.6/2.4 | 1.1 | stirring time | 17.5 hrs. at 30-35° C. | 99.94/0.06 | 99.93 | 98.7 |

As the results show, olopatadine-HCl salt formation according to applicant's process is robust and efficient. A content of the undesired E-isomer up to 2.4% could be separated from olopatadine during the HCl salt formation using 1-3 equivalents HCl and at a temperature in a range of 0° C. to 35° C. In all cases the resultant olopatadine HCl product contained less than 0.15% of the E-isomer.

What is claimed is:

1. A process for preparing olopatadine or a salt thereof, comprising:
   (a) reacting in a suitable solvent 11-oxo-6,11-dihydrodibenz[b,e]oxepin-2-acetic acid, a Wittig reagent selected from the group consisting of 3-dimethylamino-propyltriphenylphosphonium halides and salts thereof, and a base selected from the group consisting of sodium hydride, ($C_1$-$C_6$)alkyl lithium and phenyl lithium, under Wittig reaction conditions, to provide a reaction mixture containing olopatadine;
   (b) adding an amount of water sufficient to protonate residual ylide present in the reaction mixture to provide a hydrolyzed reaction mixture;
   (c) adjusting, if necessary, the pH of the hydrolyzed reaction mixture, or aqueous phase thereof, to a pH of about pH 12 or higher to convert excess 3-dimethylamino-propyltriphenylphosphonium halide, or salt thereof, into 3-dimethylamino-propyldiphenylphosphine oxide;
   (d) extracting the solution of step (c) with a suitable solvent to provide a solution containing a diastereomeric mixture of olopatadine and (E)-11-[3-dimethylaminopropylidene]-6,11-dihydrodibenz[b,e]oxepin-2-acetic acid and having a substantially reduced amount of 3-dimethylamino-propyldiphenylphosphine oxide;
   (e) adjusting the pH of the solution obtained in step (d) to a pH between about pH 4 and pH 5 to provide acid-addition salts of olopatadine and (E)-11-[3-dimethylaminopropylidene]-6,11-dihydrodibenzl[b,e]oxepin-2-acetic acid;
   (f) extracting the acid-addition salts of olopatadine and (E)-11-[3-dimethylaminopropylidene]-6,11-dihydrodibenz[b,e]oxepin-2-acetic acid with a water-mixable solvent selected from the group consisting of (i) n-butanol; and (ii) mixtures of methyl-THF and a C1-C4 alcohol; provided that if the selected solvent is a mixture of methyl-THF and a C1-C4 alcohol, then the solution is evaporated and the residue is taken up in n-butanol/water;
   (g) concentrating by azeotropic distillation the n-butanol/water solvent containing the acid-addition salts of olopatadine and (E)-11-[3-dimethylaminopropylidene]-6,11-dihydrodibenz[b,e]oxepin-2-acetic acid;
   (h) fractionally crystallizing the acid-addition salt of olopatadine;
   (i) optionally, reacting the acid-addition salt of olopatadine with a sufficient amount of a base to liberate olopatadine; and
   (j) optionally, reacting the olopatadine with a sufficient amount of an acid to convert the olopatadine into a salt of olopatadine.

2. A process for preparing olopatadine or a salt thereof, comprising:
   (a) reacting in a suitable solvent 11-oxo-6,11-dihydrodibenz[b,e]oxepin-2-acetic acid, a Wittig reagent selected from the group consisting of 3-dimethylamino-propyltriphenylphosphonium halides and salts thereof, and a base selected from the group consisting of sodium hydride, ($C_1$-$C_6$)alkyl lithium and phenyl lithium, under Wittig reaction conditions, to provide a reaction mixture containing olopatadine;
   (b) adding an amount of water sufficient to protonate residual ylide present in the reaction mixture to provide a hydrolyzed reaction mixture;
   (c) adjusting, if necessary, the pH of the hydrolyzed reaction mixture, or aqueous phase thereof, to a pH of about pH 12 or higher to convert excess 3-dimethylamino-propyltriphenylphosphonium halide, or salt thereof, into 3-dimethylamino-propyldiphenylphosphine oxide;
   (d) extracting the solution of step (c) with a suitable solvent to provide a solution containing a diastereomeric mixture of olopatadine and (E)-11-[3-dimethylaminopropylidene]-6,11-dihydrodibenz[b,e]oxepin-2-acetic acid and having a substantially reduced amount of 3-dimethylamino-propyldiphenylphosphine oxide;
   (e) adjusting the pH of the solution obtained in step (d) to a pH of from about pH 6.5 to pH 8.0 to provide a solution containing olopatadine and (E)-11-[3-dimethylaminopropylidene]-6,11-dihydrodibenz[b,e]oxepin-2-acetic acid;
   (f) extracting the solution obtained in step (e) with n-butanol to provide an n-butanol/water solution of olopatadine and (E)-11-[3-dimethylaminopropylidene]-6,11-dihydrodibenz[b,e]oxepin-2-acetic acid;
   (g) adjusting the pH of the solution obtained in step (f) to a pH of from about pH 4 to about pH 5 to provide acid-addition salts of olopatadine and (E)-11-[3-dimethylaminopropylidene]-6,11-dihydrodibenz[b,e]oxepin-2-acetic acid;
   (h) concentrating by azeotropic distillation the n-butanol/water solvent containing the acid-addition salts of olopatadine and (E)-11-[3-dimethylaminopropylidene]-6,11-dihydrodibenzl[b,e]oxepin-2-acetic acid;
   (i) fractionally crystallizing the acid-addition salt of olopatadine;
   (j) optionally, reacting the acid-addition salt of olopatadine with a sufficient amount of a base to liberate olopatadine; and
   (k) optionally, reacting the olopatadine with a sufficient amount of an acid to convert the olopatadine into a salt of olopatadine.

3. A process according to claim 1, wherein, in step (a), the Wittig reagent is combined with base to provide a reaction mixture containing 3-dimethylaminopropylidene-triphenylphosphine before adding 6,11-dihydro-11-oxo-dibenz[b,e]oxepin-2-acetic acid.

4. A process according to claim 3 wherein the base is sodium hydride.

5. A process according to claim 4, wherein about 2 to about 3 equivalents of the Wittig reagent is used.

6. A process according to claim 5, wherein the suitable solvent of step (d) is toluene or a mixture of toluene and a C1-C4 alcohol.

7. A process according to claim 6 wherein, in step (d), the solution is extracted with toluene:butanol (9:1 by volume).

8. A process according to claim 1, wherein, in the step of adjusting the pH to provide acid-addition salts of olopatadine and (E)-11-[3-dimethylaminopropylidene]-6,11-dihydrodibenz[b,e]oxepin-2-acetic acid, the pH is adjusted to a pH between 4.2 and 4.6.

9. A process according to claim 8 wherein HBr or HCl, alone or in combination, is used to adjust the pH.

10. A process according to claim 1 wherein in step (f) the acid-addition salts of olopatadine and (E)-11-[3-dimethylaminopropylidene]-6,11-dihydrodibenz[b,e]oxepin-2-acetic acid are extracted with nBuOH.

11. A process according to claim 4 wherein in step (a) the suitable solvent is THF.

12. A process according to claim 4 wherein in step (a), the Wittig reagent is combined with NaH at a temperature in the range of from about 55° C. to about 60° C. for about 2.5 hours or more before adding 6,11-dihydro-11-oxo-dibenz[b,e]oxepin-2-acetic acid to the reaction mixture.

13. A process according to claim 4 further comprising the steps of treating the olopatadine salt obtained by fractional crystallization with a sufficient amount of base to liberate olopatadine free base, and converting the olopatadine free base to a pharmaceutically acceptable salt.

14. A process according to claim 13 wherein the base is NaOH and wherein the liberated olopatadine is converted to its corresponding hydrochloride salt in acetone by adding HCl.

15. A process according to claim 14 wherein from about 1 to about 3 equivalents of HCl are used to convert the liberated olopatadine to olopatadine hydrochloride.

16. A process according to claim 14 wherein the liberated olopatadine is converted to olopatadine hydrochloride at a temperature in the range of from about 0° C. to about 35° C.

17. A method for preparing olopatadine, comprising:
   (a) combining, in a suitable solvent, a Wittig reagent selected from the group consisting of 3-dimethylamino-propyl-triphenyiphosphonium halide, or a salt thereof, with sodium hydride to provide a reaction mixture containing 3-dimethylaminopropylidene-triphenylphosphine;
   (b) combining, under Wittig reaction conditions, the reaction mixture with 6,11-dihydro-11-oxo-dibenz[b,e]oxepin-2-acetic acid to provide a diastereomeric mixture containing olopatadine or a salt thereof.

18. A method for preparing olopatadine according to claim 17, wherein the sodium hydride is present in a molar excess.

19. A method for preparing olopatadine according to claim 17, further comprising the step of adding an amount of water sufficient to protonate residual ylide remaining in the reaction mixture.

20. A method for preparing olopatadine according to claim 19, wherein the amount of sodium hydride present in the reaction mixture when step (b) is substantially complete is sufficient to provide a mixture having a pH of at least about pH 12 upon adding the amount of water sufficient to protonate the residual ylide.

21. A method for preparing olopatadine according to claim 17, wherein the solvent is THF.

22. A method for preparing olopatadine according to claim 17, wherein the temperature of the reaction mixture in step (a) ranges from about 50° C. to about 60° C.

23. A process for increasing the (Z)/(E) ratio of a diastereomeric mixture containing olopatadine or a salt thereof, comprising the steps of:
   (a) providing a solution of the diastereomeric mixture as an acid-addition salt in an n-butanol/water solvent, (b) reducing the water content to an extent sufficient to induce fractional crystallization of the olopatadine salt from solution, and, (c) isolating the crystalline olopatadine salt.

24. A process according to claim 23 wherein the diastereomeric mixture comprises olopatadine hydrobromide.

25. A process according to claim 23 wherein the reduction of water content in step (b) is provided by azeotropic distillation from a solution of n-butanol/water having a water content greater than 5%.

26. A process for increasing the (Z)/(E) ratio of an acid-addition salt of olopatadine in a diastereomeric mixture, comprising the step of stirring a suspension of the diastereomeric mixture in nBuOH containing from about 0.2% to about 4% water for an amount of time sufficient to increase the (Z)/(E) ratio of the mixture in suspension.

27. A process for increasing the (Z)/(E) ratio of a diastereomeric mixture of olopatadine, comprising beginning with a slurry of a diastereomeric olopatadine or a salt thereof in water, adjusting the pH to about the isoelectric point of olopatadine, and maintaining the slurry for an amount of time sufficient to increase the (Z)/(E) ratio.

28. A process according to claim 27 wherein the (Z)/(E) ratio of the starting material is at least about 90/10.

29. A process according to claim 27 wherein the (Z)/(E) ratio is increased from its initial ratio to a ratio of at least about 98/2.

30. A process according to claim 27 in which the pH of the mixture ranges from about pH 6.8 to about pH 7.2.

31. A process according to claim 2, wherein, in step (a), the Wittig reagent is combined with the base to provide a reaction mixture containing 3-dimethylaminopropylidene-triphenyiphosphine before adding 6,11-dihydro-11-oxo-dibenz[b,e]oxepin-2-acetic acid.

32. A process according to claim 31 wherein the base is sodium hydride.

33. A process according to claim 32, wherein from about 2 to about 3 equivalents of the Wittig reagent is used.

34. A process according to claim 33, wherein the suitable solvent of step (d) is toluene or a mixture of toluene and a C1-C4 alcohol.

35. A process according to claim 34 wherein, in step (d), the solution is extracted with toluene:butanol (9:1 by volume).

36. A process according to claim 2 wherein, in the step of adjusting the pH to provide acid-addition salts of olopatadine and (E)-11-[3-dimethylaminopropylidene]-6,11-dihydrodibenz[b,e]oxepin-2-acetic acid, the pH is adjusted to a pH between 4.2 and 4.6.

37. A process according to claim 36 wherein HBr or HCl, alone or in combination, is used to adjust the pH.

38. A process according to claim 32 wherein in step (a) the suitable solvent is THF.

39. A process according to claim 32 wherein in step (a), the Wittig reagent is combined with NaH at a temperature in the range of about 55° C. to about 60° C. for about 2.5 hours or more before adding 6,11-dihydro-11-oxo-dibenz[b,e]oxepin-2-acetic acid to the reaction mixture.

40. A process according to claim 32 further comprising treating the olopatadine salt obtained by fractional crystallization with a sufficient amount of base to liberate olopatadine free base, and converting the olopatadine free base to a pharmaceutically acceptable salt.

41. A process according to claim 40 wherein the base is NaOH and wherein the liberated olopatadine is converted to its corresponding hydrochloride salt in acetone by adding HCl.

42. A process according to claim 41 wherein from about 1 to about 3 equivalents of HCl are used to convert the liberated olopatadine to olopatadine hydrochloride.

43. A process according to claim 41 wherein the liberated olopatadine is converted to olopatadine hydrochloride at a temperature in the range of from about 0° C. to about 35° C.

44. A process according to claim 1 wherein the base in step (a) is sodium hydride.

45. A process according to claim 2 wherein the base in step (a) is sodium hydride.

* * * * *